(12) United States Patent
Mostazal

(10) Patent No.: US 11,337,886 B2
(45) Date of Patent: May 24, 2022

(54) EQUIPMENT TO ELICIT FRISSONS OR AESTHETIC CHILLS, THROUGH THE MULTISENSORIAL AND MULTIMODAL STIMULATION; WITH THE OBJECTIVE OF RELIEVING CHRONIC PAINS AND THE METHOD TO USE IT

(71) Applicant: Jorge Serani Mostazal, Las Condes (CL)

(72) Inventor: Jorge Serani Mostazal, Las Condes (CL)

( * ) Notice: Subject to any disclaimer, the term of this patent is extended or adjusted under 35 U.S.C. 154(b) by 0 days.

(21) Appl. No.: 17/389,110

(22) Filed: Jul. 29, 2021

(65) Prior Publication Data

US 2021/0361521 A1 Nov. 25, 2021

Related U.S. Application Data

(63) Continuation of application No. 16/613,165, filed as application No. PCT/CL2019/000027 on Jul. 2, 2019.

(51) Int. Cl.
*A61H 9/00* (2006.01)

(52) U.S. Cl.
CPC ... *A61H 9/0021* (2013.01); *A61H 2009/0042* (2013.01); *A61H 2201/0214* (2013.01);
(Continued)

(58) Field of Classification Search
CPC .......... A61H 9/0021; A61H 2009/0042; A61H 2201/0214; A61H 2201/0242;
(Continued)

(56) References Cited

U.S. PATENT DOCUMENTS 5,327,886 A 7/1994 Chiu
5,807,287 A * 9/1998 Cheng ................ A61H 23/0263
5/915

(Continued)

FOREIGN PATENT DOCUMENTS

CN 202822492 U 3/2013
CN 205181749 U 4/2016
(Continued)

OTHER PUBLICATIONS

Arjmand H-A, Hohagen J, Paton B and Rickard NS (2017) Emotional Responses to Music: Shifts in Frontal Brain Asymmetry Mark Periods of Musical Change. Front. Psychol. 8:2044. doi: 10.3389/fpsyg.2017.02044—13 pages.
(Continued)

*Primary Examiner* — Timothy A Stanis
*Assistant Examiner* — Matthew R Moon
(74) *Attorney, Agent, or Firm* — Hahn Loeser & Parks LLP

(57) ABSTRACT

Equipment for self-care of patients with chronic pain, through inducing, intensifying and maintaining their own frissons and where multisensory and multimodal stimuli are used to achieve it; musical, visual, aromatic and vibrotactile and cold are applied on the cutaneous surface of the spine. In addition, the method for using them through perceptual learning is presented. The equipment includes a computer and a computer system with a music and video player, lighting, presentation of aromas and a closed hydraulic circuit with a hydraulic actuator.

20 Claims, 5 Drawing Sheets

(52) U.S. Cl.
CPC ............... *A61H 2201/0242* (2013.01); *A61H 2201/102* (2013.01); *A61H 2201/1626* (2013.01); *A61H 2201/501* (2013.01); *A61H 2201/5043* (2013.01); *A61H 2201/5058* (2013.01)

(58) Field of Classification Search
CPC ...... A61H 2201/0285; A61H 2201/102; A61H 2201/1238; A61H 2201/1623; A61H 2201/1626; A61H 2201/1688; A61H 2201/501; A61H 2201/5005; A61H 2201/5012; A61H 2201/5043; A61H 2201/5048; A61H 2201/5058; A61H 2201/5061; A61H 2201/5064; A61H 2201/5082; A61H 2201/5097; A61H 23/04; A61H 2230/06; A61H 2230/30; A61H 2230/65; A61H 9/00–0007; A61H 9/005; A61H 9/0071; A61H 9/0078; A61H 9/0085; A61H 9/0092; A61F 2007/0054; A61F 2007/0056
See application file for complete search history.

(56) References Cited

U.S. PATENT DOCUMENTS

| | | | |
|---|---|---|---|
| 6,023,932 | A | 2/2000 | Johnston |
| 6,027,463 | A * | 2/2000 | Moriyasu ........... A61H 23/0236 601/46 |
| 6,425,764 | B1 | 7/2002 | Lamson |
| 6,607,499 | B1 * | 8/2003 | Becher .................. A61H 7/007 601/101 |
| 7,927,294 | B2 | 4/2011 | Kamimura et al. |
| 8,498,524 | B2 | 7/2013 | Ruiz Ballesteros et al. |
| 8,738,142 | B2 | 5/2014 | Palermo et al. |
| 8,983,278 | B2 | 3/2015 | Ruiz Ballesteros et al. |
| 9,849,206 | B1 | 12/2017 | Hsiao |
| 2002/0159916 | A1 * | 10/2002 | Whitby .................. A61L 9/035 422/4 |
| 2007/0010766 | A1 * | 1/2007 | Gil ....................... A61H 9/0078 601/96 |
| 2007/0225781 | A1 | 9/2007 | Saadat et al. |
| 2008/0269652 | A1 | 10/2008 | Reiner |
| 2009/0112134 | A1 * | 4/2009 | Avni .................. A61H 23/0263 601/15 |
| 2010/0137765 | A1 * | 6/2010 | Edelman ................. A61F 7/02 602/14 |
| 2010/0312042 | A1 | 12/2010 | Anderson et al. |
| 2011/0082384 | A1 * | 4/2011 | Harte .................. A61B 5/0002 600/557 |
| 2014/0276276 | A1 * | 9/2014 | Kurosawa .............. A61H 1/005 601/89 |
| 2015/0126802 | A1 | 5/2015 | Lim et al. |
| 2016/0175186 | A1 * | 6/2016 | Shadduck .............. A61H 19/40 601/15 |
| 2016/0198996 | A1 | 7/2016 | Dullen |
| 2016/0246944 | A1 | 8/2016 | Jain et al. |
| 2016/0263318 | A1 | 9/2016 | Osorio |
| 2017/0135407 | A1 * | 5/2017 | Cameron ................ G10L 17/00 |
| 2017/0239136 | A1 * | 8/2017 | Reader .................. A61H 1/005 |
| 2017/0303591 | A1 | 10/2017 | Cameron et al. |
| 2017/0319430 | A1 | 11/2017 | Shadduck |
| 2018/0193512 | A1 * | 7/2018 | Antonino ................ A61L 9/12 |

FOREIGN PATENT DOCUMENTS

| | | |
|---|---|---|
| DE | 102010047757 B3 | 1/2012 |
| WO | 2006084921 A1 | 8/2006 |
| WO | 2018106839 A2 | 6/2018 |
| WO | WO-2018106839 A2 * | 6/2018 ............. G16H 50/30 |

OTHER PUBLICATIONS

Arrom M. (2015): "Personality traits, coping strategies and chronic pain in patients with fibromyalgia", Tesis U. de las Baleares—22 pages.

Banos R. et al. (2012): "Positive mood induction procedures for virtual environments designed for eldery people", Interacting with Computers—8 pages.

Blakemore S. et al. (2000): "Why can't you tickle yourself?", Neuroreport vol. 11, Aug. 3, 2000—6 pages.

Blood A. J. and Zatorre R. J. (2001): "Intensely pleasurable responses to music correlate with activity in brain regions implicated in reward and emotion". PNAS, vol. 98, No. 20, Sep. 25, 2001—6 pages.

Bloomer C. et al. (2014): "Stress responses due to application of audio or visual stimuli", J. of Advanced Student Science.—16 pages.

Boehme R. et al (2018): "Distinction of self-produced touch and social touch at cortical and spinal cord level", PNAS, vol. 116, No. 6, Feb. 5, 2019—10 pages.

Brochard R. et al. (2008): "Evidence of beat perception via purely tactile stimulation". Brain Research 1223, 59-64 —6 pages.

Bushnell M. C. (2013): "Cognitive and Emotional Control of Pain and its disruption in chronic pain", Neuroscience, Advance Online Publication—26 pages.

Cacioppo J. T., Tassinary, L. G., and Berntson G. G., eds. Handbook of Psychophysiology, 2nd ed., Cambridge University Press 2007—27 pages.

Calvert G., Spence C. and Stein B. Eds. (2004): "The Handbook of Multisensory Processes", Massachusetts Institute of Technology—30 pages.

Chang YC. et al. (2015): "Short-term effects of self-massage combined with home exercise on pain, daily activity, and autonomic function in patients with myofascial pain dysfunctions syndrome.", J. Phys Ther. Sci. 27: 217-221—5 pages.

Cheng X. et al. (2017), "On-stream analysis of iron ore slurry using laser-induced breakdown spectroscopy", Applied Optics, vol. 56, No. 33—6 pages.

Chesterton LS. et al. (2002): "Skin Temperature Response to Cryotherapy". Arch Phys Med Rehabil, vol. 83—7 pages.

Colver M. and El-Alayli (2015): "Getting aesthetic chills from music: The connection between openness to experience and frisson", Psychology of Music—16 pages.

Costa P. (2015): "Modelling fragrance components release from a simplified matrix used in toiletries and household products", Industrial & Engineering Chemistry Research, just accepted manuscript, doi: 10.1021/acs.iecr.5b03852—32 pages.

Craig D. G. (2005): "An exploratory study of physiological changes during "chills" Induced by music.", Music. Sci., vol. IX, No. 2, pp. 273-287—15 pages.

De Kort Y. et al. (2006): "What's wrong with virtual trees? Restoring from stress in a mediated environment", Journal of Environmental Psychology 26, pp. 309-320—14 pages.

DeLeon I. and Iwata B. (1996): "Evaluation of a Multiple-Stimulus Presentation Format for Assessing Reinforcer Preferences", J. of Applied Behavior Analysis, vol. 29, No. 4, pp. 519-533—15 pages.

Diette G. at al (2003): "Distraction Therapy With Nature Sights and Sounds Reduces Pain During Flexible Bronchoscopy", Synopsis, Key Point Summary, Chest, vol. 123, No. 3, pp. 941-948—2 pages.

Dobek C. E. et al. (2014): "Music modulation of pain perception and pain-related activity in the brain, brainstem, and spinal cord", Journal of Pain, doi: 10.1016/j.jpain.2014.07.006—37 pages.

Eckart S. (1974): "Temperature Regulation: The Spinal Cord as a Site of Extrahypothalamic Thermoregulatory Functions", Rev. Physiol. Biochem. Pharmacol., vol. 71∫76 pages.

Edris A. (2007): "Pharmaceutical and Therapeutic Potential of Essential Oils and Their Individual Volatile Constituents: A Review". Phytotherapy Research, 21, doi: 10.1002/ptr—17 pages.

Edwards C. et al. (2017): "Neurostimulation Devices for the Treatment of Neurologic Disorders", Mayo Clinic Proceedings, Symposium on Neurosciences, vol. 92, No. 9, pp. 1427-1444—18 pages.

(56) References Cited

OTHER PUBLICATIONS

Ernst E. and Fialka V. (1994): "Ice freezes Pain?; A Review of the Clinical Effectiveness of Analgesic Cold Therapy", J. of Pain and Symptom Management, vol. 9, No. 1, pp. 56-59—4 pages.

Etzi R. et al. (2018): "Stroking and tapping the skin: Behavioral and electrodermal effects", Experimental Brain Research, doi: 10.1007/S00221-017-5143-9—31 pages.

Fernandez-Sotos A. et al. (2016): "Influence of Tempo and Rhytmic Unit in Musical Emotion Regulation", Frontiers in Computational Neuroscience, August, vol. 10—13 pages.

Field T. (2017) "Massage therapy research review", Complement Ther Clin Pract, Aug. vol. 24, pp. 19-31, doi: 10.1016/j.ctcp.2016.04.005—30 pages.

Follman R. et al. (2018): "Multimodal sensory information is represented by a combinatorial code in a sensorimotor system", PLOS Biology, vol. 16, No. 10—31 pages.

Fridja, N. (1994). "Moods, Emotion Episodes, and Emotions." En P. Ekman, y R. J. Davidson, (editors). The Nature of Emotion. Oxford University Press: New York.—6 pages.

Garza-Villarreal E. et al. (2017): Music-Induced Analgesia in Chronic Pain Conditions: A Systematic Review and Meta-Analysis, Pain Physician, vol. 20, pp. 597-610—14 pages.

Gay-Balmaz and Putkaradze V. (2018) "Geometry theory of flexible and expandle tubes conveying fluid: equations, solutions and shock waves." Physics, Flu-Dyn.—36 pages.

Gladwell V. et al. (2012) "The effects of views on nature and autonomic control", Eur. J. Appl. Physiol. 112, doi: 10.1007/s00421-012-2318-8—9 pages.

Gold J L. and Watanabe T. (2010): "Perceptual Learning", Curr Biol., Jan., vol. 20, No. 2, doi: 10.1016/j.cub.2009.10.066—4 pages.

Goldstein S. and Casanelia L. (2010): "Foundations of Massage", Chap. 16—The Techniques of Swedish Massage, Lisa Casanelia and David Stelfox, 3 Ed. Editors Churchill and Livingstone, Elsevier, pp. 163-184—22 pages.

Goldstein, A. (1980): "Thrills in response to music and other stimuli". Physiological Psychology, vol. 8, No. 1, pp. 126-129—4 pages.

Grewe O. et al. (2007): "Listening to music as a re-creative process: Physiological, psychological and psychoacoustic correlates of chills and strong emotions", Music Perception, vol. 24, No. 3, pp. 297-314—19 pages.

Grewe O. et al. (2010): "Chills in different sensory domains: Frisson elicited by acoustical, visual, tactile and gustatory stimuli". Psychology of Music, vol. 39—21 pages.

Grinde B. and Grindal G. (2009): "Biophilia: Does Visual Contact with Nature Impact on Health and Well-Being?", Int. J. Environ. Res. Public. Health, vol. 6, pp. 2332-2343, doi: 10.3390/ijerph6092332—12 pages.

Gross, J.J. & Thompson, Ross. (2007). Emotion Regulation: Conceptual Foundations. Handbook of Emotion Regulation. 3-27.—23 pages.

Hanjalic, K. and Launder, B.E. (1976) "Contribution towards a Reynolds-stress closure for low-Reynolds-number turbulence", J. Fluid Mech., vol. 74, part 4, pp. 593-610—19 pages.

Harrison, L. and Loui, P. (2014): "Thrills, chills, frissons and skin orgasms: toward an integrative model of transcendent psychophysiological experiences in music". Frontiers in Psychology, vol. 4, art 790—7 pages.

Harvey L. (1992): "The Critical Operating Characteristic and the Evaluation of Expert Judgment", Organizational Behavior and Human Decision Processes, vol. 53, pp. 229-251—23 pages.

Haze S. et al. (2002): "Effects of fragrance inhalation on sympathetic activity in normal adults", Jpn. J. Pharmacol., vol. 90, pp. 247-253—7 pages.

Hilgard, E.R. (1988) "Review of B. F. Skinner's The Behavior of Organisms", Journal of the Experimental Analysis of Behavior, vol. 50, No. 2, September, pp. 283-286—4 pages.

Holden R and Holden J. (2013): "Out of Hours Music: a better alternative than pain?", British Journal of General Practice, Oct., p. 536.

Holmes, N., Calvert, G. and Spence, C. (2009) Multimodal integration. In: Binder, M. D., Hirokawa, N. and Windhorst, U. (eds.) Encyclopedia of Neuroscience. Springer. ISBN 9783540237358, pp. 2457-2461—10 pages.

Huang J. et al. (2013): "Feeling Music: Integration of Auditory and Tactile Inputs in Musical Meter Perception", Adv Exp Med Biol, vol. 787, pp. 453-461, doi: 10.1007/978-1-4614-1590-9_50—24 pages.

James K.H. et al. (2018):"The Handbook of Multimodal Multisensory Interfaces vol. 1: Foundations and User Modeling and Modeling and Common Modality Combination", Ed. Morgan and Claypool, p. 51-94—44 pages.

Juslin P. N. and Vastfjall D. (2008): "Emotional responses to music: The need to consider underlying mechanisms", Behavioral and Brain Science, vol. 31, pp. 559-621—64 pages.

Juslin P.N. et al. (2008): "An Experience Sampling Study of Emotional Reactions to Music: Listener, Music and Situation.", Emotion, vol. 8, No. 5, pp. 668-683—17 pages.

King, A.J. (2005). Multisensory Integration: Strategies for Synchronization. Current biology : CB. 15. R339-41. 10.1016/j.cub.2005.04.022.—4 pages.

Koelsch S. and Jancke L. (2015): "Music and the heart", European Heart Journal, vol. 36, No. 44, pp. 3043-3049, doi: 10.193/eurheartj/ehv430—8 pages.

Koole S. (2009): "The psychology of emotion regulation: An integrative review", Cognition and Emotion, vol. 23, No. 1, pp. 4-41—39 pages.

Lakhan S. et al. (2016): "The Effectiveness of Aromatherapy in Reducing Pain: A systematic Review and Meta-Analysis", Pain Research and Treatment, vol. 2016, article ID 8158693—14 pages.

Lee J. et al (2011): "Effect of forest bathing on physiological and psychological responses in Young Japanese male subjects", Public Health, vol. 125, pp. 93-100—8 pages.

Lee, Jin Hyung (2016): "The effects of Music on Pain: A Meta-Analysis", Journal of Music Therapy, vol. 53, No. 4, pp. 430-477—49 pages.

Louis M. and Kowalsky S. (2002): "Use of aromatherapy with hospice patients to decrease pain, anxiety, and depression and to promote and increased sense of well-being." Am J. Hosp. Pall. Care, vol. 19, No. 6, Nov./Dec., pp. 381-386—6 pages.

M M Tse et al. (2002): "The effect of visual stimuli on pain threshold and tolerance", J. of Clinical Nursing, vol. 11, pp. 462-469—8 pages.

Malamud-Kessler C, et al. (2014) "Physiology of vibration sense", Rev Mex Neuroci. vol 15, No. 3, pp. 163-170.—11 pages.

McGlone, F. et al. (2014) "Discriminative and Affective Touch: Sensing and Feeling", Perspective, vol. 82, No. 4, pp. 737-755—19 pages.

Melzack R. and Wall P. (1965): "Pain mechanisms: a new theory", Science, vol. 150, No. 3699, pp. 971-979—9 pages.

Mills S. et al. (2016): "Identification and Management of Chronic Pain in Primary Care: A Review", Curr Psychiatry Rep, vol. 18, No. 22—9 pages.

Monteiro ER et al. (2017): "Self-massage and Autonomic Response: Future Direction", Journal of Exercise, Sport and Orthopedics, vol. 4, No. 2, pp. 1-3—4 pages.

Noy D. et al. (2017): "Audiovisual integration increases the intentional step synchronization of side-by-side walkers", Human Movement Science, vol. 56, pp. 71-87—17 pages.

Onyesolu, Moses & Eze, Udoka (2011): "Understanding Virtual Reality Technology: Advances and Applications", Advances and Applications. DOI: 10.5772/15529—20 pages.

Park B. and Kim S. (2013): "Cooling the Skin: Understanding a Specific Cutaneous Thermosensation", Journal of Lifestyle Medicine, vol. 3, No. 2, pp. 91-97—7 pages.

Piaget J. (1947): "The formation of the symbol in the child imitation, play and dream, image and representation". Fund of Economic Culture, Mexico-Buenos Aires—24 pages.

Plutchick R. and Kellerman H. (1980): "Emotion: Theory, Research, and Experience", book review in The American Journal of Psychology, vol. 94, No. 2—4 pages.

(56) References Cited

OTHER PUBLICATIONS

Poenaru D. et al. (2016): "Local Application of Vibration in Motor Rehabilitation: Scientific and Practical Considerations", MAEDICA—J of Clinical Medicine, vol. 11, No. 3, pp. 227-231—5 pages.
Rastogi A. (2018): "Physiological effects of cryotherapy: A systemic Review", Indian J. of Applied Research, vol. 8, No. 5—4 pages.
Recanzone G. (2009): "Interactions of Auditory and Visual Stimuli in Space and Time", Hear Research, Dec. 2009, vol. 258, No. 1-2, pp. 89-99, doi: 10.1016/j.heares.2009.04.009—28 pages.
Reynolds, Osborne (1895): "On the Dynamical Theory of Incompressible Viscous Fluids and the Determination of the Criterion." Philosophical Transactions of the Royal Society of London. A, v. 186, downloaded from https://royalsocietypublishing.org on Jul. 10, 2021—42 pages.
Rodica F. et al (2011): "Emotions induced by operatic music: Psychophysiological effects of music, plot and acting, A scientist's tribute to Maria Callas", Brain and Cognition, vol. 76, pp. 146-157—12 pages.
Rolston A. and Lloyd-Richardson (2018): "What is emotion regulation and how do we do it ?," Cornell Research Program on Self-Injury and Recovery—5 pages.
Roy M. et al. (2008): "Emotional Valence Contributes to Music-Induced Analgesia", Pain, vol. 134, pp. 140-147—8 pages.
Salimpoor V. et al. (2009): "The Rewarding Aspects of Music Listening Are Related to Degree of Emotional Arousal", PLoS ONE, vol. 4, No. 10: doi: 10.1371/journal/pone.0007487—14 pages.
Sawkut R. et al. (2010): "Learning Theories: A Review", Oxford Business and Economics Conference Program—11 pages.
Schneider R. et al. (2018): "Medical aromatherapy revisited—Basic mechanisms, critique and a new development", Hum. Psychopharmacol. Clin Exp., https://doi.org/10.1002/hup.2683—11 pages.
Seah S. and Griffin M. (2006): "Normal values for the thermotactile and vibrotactile threshold in males and females" Int Arch Ocupp Environ Health, May 2008, doi: 10.1007/S00420-007-0252-6—52 pages.
Sena K. (2013): "A Systematic Review on the Neuronal Effects of Music on Emotion Regulation: Implications for Music Therapy Practice." Journal of Music Therapy, vol. 50, No. 3, pp. 198-242—46 pages.
Sergeant DC and Himonides E (2016): "Gender and Music Composition: A Study of Music, and the Gendering of Meanings", Frontiers of Psychology, vol. 7, article 411—15 pages.
Shademan M. et al. (2012) "CFD Study of Effects of Geometry Variations on Flow in a Nozzle," Engineering Applications of Computational Fluid Mechanics, vol. 6, No. 3, pp. 412-425—15 pages.
Shahrbanian S. et al. (2012): "Use of virtual reality (immersive vs non immersive) for pain management in children and adults: A systematic review of evidence from randomized controlled trials". Pelagia Research Library, European Journal of Experimental Biology, vol. 2, No. 5, pp. 1408-1422—15 pages.
Shaygan M. et al. (2017): "Valence and arousal value of visual stimuli and their role in the mitigation of chronic pain: What is the power of pictures?" J. of Pain, vol. 18, No. 2, doi: 10.1016/j.jpain.2016/10.007—33 pages.
Simons L.E. et al (2014): "Psychological processing in chronic pain: A neural systems approach", Neurosci. Biobehav. Rev. http://dx doi.org/10.1016/j.neubiorev.2013.12.006—18 pages.
Smith K. and Zhu L. (2010): "Theoretical evaluation of a simple cooling pad for inducing hypothermia in the spinal cord following traumatic injury", Med. Biol. Eng. Comput. vol. 48, pp. 167-175, https://doi.org.10.1007/s11517-009-0543-z—9 pages.
Sowndhararajan K. and Kim S. (2016): "Influence of Fragrances on Human Psychophysiological Activity: With Special Reference to Human Electroencephalographic Response", Sci. Pharm., vol. 84, pp. 724-751, doi: 10.3390/scipharm84040724—28 pages.
Subramanian, R. S. (2015). Heat transfer in flow through conduits. Department of Chemical and Biomolecular Engineering, Clarkson University Project.
Sutton S. et al. (1965): "Evoked-Potential Correlates of Stimulus Uncertainty", Science, vol. 150, November, pp. 1187-1188—2 pages.
Takabatake S. et al. (1988); "Peristaltic pumping in circular cylindrical tubes: a numerical study of fluid transport and its efficiency", J. Fluid Mech., vol. 193, pp. 267-283—17 pages.
Tang N. et al. (2008): "Effects of mood on pain responses and pain tolerance: An experimental study in chronic back pain patients", Pain, vol. 138,m pp. 392-401—10 pages.
Triberti S. et al. (2014): "Psychological factors influencing the effectiveness of virtual reality-based analgesia: A systematic review", Cyberpsychology, Behavior, and Social Networking, vol. 17, No. 6, doi: 10.1089-cyber.2014.0054—12 pages.
Turk D. and Wilson H. (2010): "Fear of Pain as a Prognostic Factor in Chronic Pain: Conceptual Models, Assessment, and Treatment Implications", Curr. Pain. Headache. Rep., April, vol. 14, No. 2, pp. 88-95, doi: 10.1007/s11916-010-0094-x—13 pages.
Uher I. et al. (2018): "Vibration Therapy and its Influence on Health", Biomed J Sci & Rec Res, vol. 6, No. 5, doi: 10.26717/BJSTR.2018.06.001406—5 pages.
Uhlig S. et al. (2013): "Effects of Music on Emotion Regulation: A Systematic Literature Review". Proceedings of the 3rd International Conference on Music and Emotion (ICME3), Jyvaskyla, Finland, Jun. 11-15, 2013, Luck and Brabant, eds.—5 pages.
Ulrich R. S. et al. (1991), "Stress recovery during exposure to natural and urban environments", J. Environ. Psychology, vol. 11, pp. 201-230—31 pages.
Verduyn, P. et al. (2012) "Determinants of the shape of emotion intensity profiles", Cognition and Emotion, vol. 26, No. 8, pp. 1486-1495, doi: 10.1080/02699931.2012.662152—11 pages.
Verduyn, P., & Lavrijsen, S. (2015). "Which emotions last longest and why: The role of event importance and rumination", Motivation and Emotion, vol. 39, No. 1, pp. 119-127—9 pages.
Vuoskoski J. and Eerola T. (2011): "The role of mood and personality in the perception of emotions represented by music", Cortex, vol. 47, pp. 1099-1106—8 pages.
Wilcox D. C. (2008): "Formulation of the k-omega Turbulence Model Revisited", AIAA Journal, vol. 46, No. 11, doi: 10.2514/1.36541—16 pages.
Yuan-Chi Lin et al. (2017): "Using Integrative Medicine in Pain Management an Evaluation in Pain Management: An Evaluation of Current Evidence", Anesth. Anal; vol. 125, No. 6, pp. 2081-2093—13 pages.
Zatorre R and Salimpoor V. (2013): "From perception to pleasure: music and its neural substrates", PNAS, vol. 110, suppl 2, pp. 10430-10437, www.pnas.org/cgi/doi/10.1073/pnas.1301228110—8 pages.
Zentner M., Grandjean D. and Scherer K. (2008): "Emotions Evoked by Sound of Music: Characterization, Classification and Measurement". Emotion, vol. 8, No. 4, pp. 494-521, doi: 10.1037/1528-3542.8.4.494—29 pages.

\* cited by examiner

EQUIPMENT TO ELICIT FRISSONS OR AESTHETIC CHILLS, THROUGH THE MULTISENSORIAL AND MULTIMODAL STIMULATION; WITH THE OBJECTIVE OF RELIEVING CHRONIC PAINS AND THE METHOD TO USE IT

CROSS-REFERENCE TO RELATED APPLICATIONS

This application claims priority to, and the benefit of, U.S. patent application Ser. No. 16/613,165 filed on 13 Nov. 2019 with the United States Patent Office, which is a national stage entry of International PCT Application Ser. No. PCT/CL2019/000027 filed on 2 Jul. 2019, the contents of which are both hereby incorporated by reference in their entirety.

FIELD OF INVENTION

This invention provides the equipment and how to use it, for the self-care of patients with chronic pain, by inducing and/or intensifying and/or maintaining their own frissons, by means of multisensory and multimodal stimulations. Among the individual and social benefits provided by this invention is to improve the individual's, family and work life of patients by decreasing the cost of medical treatments, without producing habituation and reducing adverse side effects.

INTRODUCTION

The ultimate goal of this invention is to make patients with chronic pain reassure that they are able to regain the ability to have it under control, since ignorance about what is happening to them and feelings of helplessness exacerbate anxiety and fear. Holden R and Holden J. (2013).

The standard definition of chronic pain given by the International Association for the Study of Pain is one that persists beyond normal pain for a tissue over time. In an arbitrary way a chronic pain has been defined as that which lasts more than 12 weeks after a continuous acute pain. At a medical level the difference between acute and chronic pain, is that in which acute pain the goal of the treatment pointed to the causes of it, while in chronic pain the goal is to direct attention to its effects in order to maximize the functionality and the patient's quality of life.

It is estimated that worldwide one thousand five hundred million people suffer from chronic pain and that around 100 million north americans suffer from it, with an important effect on the economy. In this last country the loss of productivity attributable to this type of pain is estimated at around $299 and 325 billion annually, due among other factors to the lost work hours of the patient as well as that of the people related to it.

According to Mills S. et at (2016), chronic pain is a common, complex and challenging condition, where to deal with it with good results requires understanding the biological, social, physical and psychological context of the individual. Simons L. et al (2014), argue that chronic pain involves complex brain circuits that include sensory, emotional, cognitive and interoceptive processing, which in rigour is a another pathology, since it causes changes in the nervous system that aggravate it (comorbidity).

According to the bibliographic review the authors Bushnell M. C. et al (2013), pain is a sensory and emotional experience that can vary widely among people, and even in the individual, depending on the context and meaning of the pain and the psychological state of the person. Cognitive and emotional factors, such as anxiety and fear, have an important influence on the perception of pain.

Pain can have negative effects on emotions and cognitive functions. A negative emotional state can lead to an increase in pain, while a positive one can reduce it. Similarly, cognitive states such as attention and memory can increase or decrease pain. Certainly emotions and cognition can interact with each other.

In general terms, the pain that affects patients with chronic pain can be classified as:

Nociceptive pains: Pains whose etiology is an inflammation or continuous peripheral damage. This type of pain may respond to medications or procedures.

Neuropathic pains: Pains caused by trauma to the peripheral nerves. This pain can respond to pharmacotherapy.

Central pains: This type of pain can be constant and goes from moderate to severe and is due to damage in the CNS that causes a sensitization of the pain system. This type of pain can respond well to psychotropics and therapies without opioids.

Staff of the Mayo Clinic notes that the appropriate medications for chronic pain, and that are part of the treatments of conventional medicine, are the following (Steps I to II of WHO):

| Type of medication | How do they work | Pains |
|---|---|---|
| (Non Steroids Anti-inflammatories | Block enzymes COX-1 y COX-2 related with pain and inflamation. | Mild to moderate from swelling and inflammation. Arthritis, muscular sprains, neck and back injuries. |
| Paracetamol or Acetaminophen | Probably they block COX-3 enzyme | Mild to moderate pains |
| Selective inhibitors of Cyclooxygenase | Probably they block COX-2 enzyme. | Rheumatoid arthritis, osteoarthritis and pain of injuries. |
| Antidepressants | They affect chemical processes that cause pain. | Dolor neuropático dolores de cabeza crónicos, fibromialgia y lumbalgia crónica |
| Seizure drugs | Relieve pain caused by damage to nerve fibers | Neuropathic pain, chronic headaches, fibromyalgia and chronic low back pain |
| Opiods | Activate neurotransmitters, endorphins, which reduce pain and increase well-being | Acute pain such as post-operative or bone fractures. |

An alternative to the use of medications for chronic pain relief is the use of neurostimulation therapies (WHO Step IV), which include invasive and non-invasive methods. In those treatments, electromagnetic energy is applied to specific anatomical targets to elicit the neurostimulation of the network of neural circuits. Authors Edwards C. et al (2017) made a literature review in which they present three devices of this type of apparatus; of deep stimulation of the brain, of motor cortex stimulation and of vagus nerve stimulation.

All these implantable systems include three primary components: the electrode, the extension and the pulse generator. The electrode is implanted in the target area, the extension subcutaneously connects the electrode to the pulse generator, which also provides the electrical energy (batteries) to the device. The pulses interfere and block the electrical signals that cause the pain, an effect that is based on the Gate Control Theory; of the authors Melzack R and Wall P. (1965).

Although pharmacological treatments have been used frequently for the relief of chronic pain, among others opiates ones, there is reluctance to use them in the latter time in non-cancerous patients, due to problems in their tolerance, dependence, addiction and its high costs. It's for these reasons that the interest in using integrative medicinal strategies in the treatment of chronic pain has increased.

The authors Yuan-Chi Lin et al (2017), made a literature review, in which 1686 publications about integrative medicinal therapies could be identified, for the treatment of chronic pain, which includes nutritional supplements, yoga, relaxation, Tai Chi, massage, spinal manipulation, acupuncture and others.

The literature review shows evidence of a positive, although moderate, effect of yoga, of relaxation, of Tai Chi, massages and spinal manipulation and a solid backing of acupuncture, as complementary medicine, which reduces the use of opioids.

STATE OF THE ART

Multisensorial and Multimodal Stimulation

According to Holmes N. et al (2009), multisensory stimulation refers to the combination of information from different sensory modalities (the five classic ones: vision, hearing, touch, taste and smell), as well as some less obvious ones such as proprioception, the kinesthetic, pain and vestibular sense, which gives rise to the changes associated with the perception and reception of those stimuli.

Laird D. (1985) observed that in learning, there is an asymmetry in the information provided by the senses, since most of the knowledge reported by adults acquired it through vision (75%), through hearing (13%) and by the remaining senses (12%). According to Sawkut R. (2010), it is understood that learning is a process by which a subject increases its knowledge reserves and uses that knowledge to adapt to the environment.

When talking about multisensory stimulation, reference is made to the entry of information through the senses to elaborate sensations and perceptions, the first element on which learning is built, and which involves the first stage of the development of basic cognitive functions, to which follows then the development of higher cognitive functions.

Multimodal perception deals with how at some point of perceptual processing, in which sensations are selected, organized and interpreted, in it information coming from various sensory modalities is integrated. According to Follman R. et al (2018), the information captured by the senses is first integrated separately and then combined in various multimodal convergence zones, including the cortical and subcortical regions and also in the multimodal association zones.

It has been shown that responses to an integral multimodal stimuli are greater than the sum of individual unimodal responses. Calvert et al (2004) demonstrated how stimuli that individually presented are weak and ineffective can be combined in a superaditive way, giving rise to more intense and rich multisensory experiences than the linear combination of the individual parts. Multimodal stimulation is often used in the rehabilitation of patients who have had recent brain damage.

According to James K. et al (2018), the mechanisms that support multimodal-multisensory learning nowadays are is being better understood, since they has multiple benefits, including the incorporation of isolated neural networks that then serve as a link to create more efficient adaptive systems.

The fact that interacting with the environment involves multisensory as well as multimodal processing, makes that that interaction facilitates learning in many other domains, including pain management, through emotional regulation and understanding of cognitive processes. In this invention the multisensory and multimodal presentation of the following types of stimuli and their responses is described: a) Music therapy, b) Visual stimuli, c) Vibrotactile stimuli, b) Cold therapy and c) Aromatherapy.

Music Therapy

According to the American Association of Musical Therapy (AMTA), music therapy consists of using music in a therapeutic way, aimed at improving the functional physical, psychological, cognitive and/or social aspects of patients. Furthermore, music therapy interventions can be designed to promote well-being, manage stress, relieve pain, express feelings, improve communication and promote physical rehabilitation. It is said that music is not only heard but felt in the body, which suggests that there are other senses involved in the experience, in addition to hearing, as well as proprioception, the vestibular system and/or cutaneous touch.

Music is differentiated by tone and timbre, however it's also distinguished by the processing of the sequence of notes, giving rise to rhythm, tempo and metrics. Brochard. R. et al (2008) assumed that people could not extract the structure of the metric, through vision and through light flashes, however through an experiment they were able to demonstrate that people were able to extract the metric from a tactile stimulation (tingling of the fingertips).

Huang J. et al (2013), did an experiment to demonstrate that the stimuli of the skin afferents that innervate the skin and the deep tissues of the body, contribute to the perception of the metric. The participants had to discriminate between 2 sequences, one of 2 pulses (like the marches) and another of 3 (waltz). The stimuli were presented to them in three different ways: 1) unimodal (hearing and touch separately), 2) Different combinations of bimodal inputs that were distributed between the auditory and tactile channels and 3) Simultaneous bimodal inputs in which the two channels contained passwords metric congruent or incongruent.

Huang et al demonstrated first that the metric is well perceived, from 70 to 85%, when the tactile or auditory keys were presented separately since in the bimodal inputs the tactile and auditory keys were integrated to produce percepts (products of artistic excellence) metric coherent In addition, a high performance was observed, 70 and 90%, when all the important notes of the metric were assigned to a single channel and reduced to 60% when half of the notes were assigned to the remaining one. By simultaneously presenting the notes in both channels, congruent keys improved recognition by up to almost 90%. These results are the first demonstration of the cross-sensory perception and the most probable thing is that the metric comes from a single nervous path, which is fed with information from both systems, but where the auditory information has a greater weight.

Music and Pain

A meta-analysis, regarding the effect of music on pain, made by Hyung J. (2016), included the results of 97 researches published between 1995 and 2014, obtained from 12 databases and from other sources, and It yielded the following results:

Music decreased pain, by around 1.13 units, on a scale of 1 to 10.

The music had a moderate effect in reducing the levels of analgesics, both opioids and non-opioids, during or after the administration of the same.

The results showed a statistically significant effect that music decreases heart and respiratory rates and systolic blood pressure.

Hyung J. concluded that musical interventions are an effective complementary medicine for the relief of pain, both acute and chronic.

On the other hand the authors Garza-Villarreal et al (2017) argue that although music is used increasingly for the management of chronic pain (efficient, low cost and non-invasive), but there are few clinical backgrounds on its application in patients with chronic pain, so they chose to do a literature review and a meta-analysis considering all the published studies that dealt with musical interventions for chronic pain made up to May 2016. (768).

Garza-Villaroel et al concluded that music decreased self-reported pain, anxiety and symptoms of depression, in conditions of chronic pain. They also observed that self-selected music had a greater analgesic effect than that offered by researchers. This would be the most complete bibliographical review and meta-analysis, regarding the relationship chronic pain music, made up to that date The authors C. E. Dobek et al (2014) affirm that pain is a very subjective experience that can be mitigated by listening to music and that corresponds to a phenomenon known as music-induced analgesia. There would be abundant literature demonstrating that music can reduce stress, depression and anguish in people with acute or chronic pain, however its mechanism of action has not yet been demonstrated, although it has been observed that pleasant emotions reduce pain and that the unpleasant increase it. These results cannot be explained only by the distraction effect, since the negative emotional stimuli, although they also have a distracting effect, do not diminish the pain. Following this logic, the authors studied the modulating effect in pain of positive and negative emotional reactions of music.

The authors Roy M. et al (2008), maintain that the ability of music to calm has been used in many traditional forms of medicine. As an example, they cite a pioneering work done with 5000 dental surgery patients, where 90% of them reported that the pain had been reduced with music. Another effect of the analgesic properties of music is to induce strong positive emotions, since it has been observed that they improve mood and influence a wide range of cognitive abilities. Hence, emotional reactions can be a key component in explaining music-induced analgesia.

In US patent 2010/0312042 A1 it is held that music therapy was administered by professional specialists to patients on an individual basis, however the delivery of this therapy was limited by the number of specialists, especially in health institutions. In order to overcome this limitation, they created a system and a method for administering therapeutic music contents individually, according to a pre-scribed sequence and according to the preferences of the patients and the schedules of the daily activities.

The CN 202822492U utility model discloses a multifunctional therapeutic electromusical stimulation device that combines acupuncture, moxibustion technology (heating body points) and music therapy technology. The multifunctional therapeutic apparatus comprises an output circuit, a storage unit, an audio decoder unit, a signal processing unit, a main control unit, an A/D conversion unit, an audio amplification unit and a volume and power regulation unit and where the output circuit is connected to a therapeutic electrode that is applied to the body through pulses. The storage unit stores music files that are used according to a therapeutic prescription.

Music and Emotions

Jusin P. et al (2008), did a study to investigate emotional reactions in daily life, with and without music. To avoid the use of self-reports, participants were given notebooks that issued random warnings during the day, with each warning they had to report their situation and their emotional state. When comparing the emotional states reported by the participants with or without daily music, the results revealed that their emotional states were more positive with the presentation of music. The authors conclude that music induces emotions and that it can be done on a daily basis.

Juslin P. and Vastfjall D. (2008), proposed 6 mechanisms, other than cognitive evaluation, through which music would induce emotions and that are the following:

a) Reflexes of the brainstem when a loud and/or unexpected sound causes a reflex response, b) Evaluative conditioning, which occurs when a piece of music is associated with an emotional event or object, c) Emotional contagion when the emotion expressed by music is internalized, d) visual images evoked by music that can have an emotional connotation, e) episodic memory that is related to autobiographical events and f) frustration in the fulfillment of musical expectations.

Zentner M. and Grandjean D. and Scherer K. (2008), conducted several experiments using self-reports to examine the emotions most commonly experienced by the public during various musical events. In the third of those experiments, 2002 attendants to different types of concerts were recruited to answer a questionnaire indicating which affective state, from a list of 65 possible ones, was the one they had perceived most frequently in the events. Of the 801 that returned their questionnaires, the affective state they had experienced most frequently was relaxation (44.6%), happiness (41.5%) and joy (39%), respectively. The last ones were anger (with 2.4%), depression (2.7%) and distress (3.4%).

Based on this information, Zetner el al concluded that the excitation effect of music can be differentiated empirically in many subunits (they determined 40 affective states), which grouped into 9 emotions: delight, nostalgia, transcend, peace, tenderness, energy, joy, tension and sadness and in 3 big factors, sublime, vitality and upset. In summary, it is concluded that positive emotions are the most frequently experienced in musical events.

Music and Emotion Regulation

Rolston A. and Lloyd-Richardson (2018), hold that emotional regulation is a term used to describe a person's ability to regulate the valence, intensity or duration of an emotional experience. According to Koole S. (2009), making use of emotional regulation people can Increase, maintain or mitigate positive or negative emotions.

Sena K. (2013), conducted a systematic review on emotional regulation (ER), which is an internal process in which the person maintains a comfortable state of excitement, while regulating one or more aspects of the emotion. The objectives of the literature review were to explore and synthesize, what is known about how music and musical experiences impact on the neural structures related to ER. In addition to considering the implications of these findings to structure the presentation of stimuli that facilitate ER; In short, find the way to use music to enhance emotional regulation.

The results obtained by Sena indicate that there are certain musical characteristics and experiences that cause patterns of desired and unwanted neuronal activation related to ER. The desired activation patterns occur when listening to favorite and familiar music and also when singing and in the musicians when improvising. Unwanted activation patterns arise when complex, dissonant and unexpected musical events occur.

Various techniques have been used to evaluate the regulation of emotions such as self reports, neuroimaging and psychophysiological measurements, however studies have been limited by the number of strategies used; where by emotion regulation strategy is understood the way to manipulate them. The strategies generally used in the various studies in this regard are those formulated by Gross J. and Thompson R. (2007): Selection of the situation, development of skills, distraction, breathing, emotional expression, social support and suppression of emotions. Other authors suggest that individuals may have a greater number of strategies to choose and match them within a given context.

The authors Verduyn P. and Lavrijsen S. (2015), point out that emotions are dynamic processes that change over time. A determining feature of emotions is the duration of the experience, which has been defined as the amount of time that elapses between the beginning and end of an emotional episode. The beginning and end of an emotional episode can be identified relatively easily, since unlike the state of mind that is less specific, less intense, more durable and less given to be activated by a given stimulus, emotions begin with an external and internal event. It has been observed that the duration of emotions is highly variable, where there are some that last a couple of seconds and others that last for hours or more. While sadness tends to last a long time, shame, disgust and fear tend to last a short time.

Verduyn et al (2012), affirm that a characteristic of emotions is their intensity and that during an emotional episode the intensity varies, giving rise to a profile of intensity over time which can have different forms and where the variability of the intensity profile of the emotion can be described by three functional characteristics; the inclination at the beginning of the emotion (slope), the asymmetries in the profile and the number of maxima. However, it is not clear what are the factors that determine the variability of each of these characteristics.

Music and Frissons

Frissons known as aesthetic musical chills are a psychophysiological response to a gratifying auditory and/or visual stimulus that induces a pleasant affective state or otherwise said of a positive valence. The frisson are characterized by the chills that cause, in some cases by piloerection and pupil dilation and are studied by psychology and neuroscience. However unlike the chills in the frissons there are trembles and great emotional intensity. The frisson implies a pleasant but variable sensation, since it affects different parts of the body, depending on the person and the circumstances of the induction and that comprises sensorial, affective biological, and psychological components similar to those of a sexual orgasm.

Grewe O. et al (2010) presented evidence that frissons can be provoked by auditory, visual, tactile or gustatory stimulation and could even be provoked by mental self-stimulation (without external stimuli). They did an experiment in which in which the participants were presented with 73 stimuli (23 images, 23 sounds, 23 music, 2 tactile and 2 gustatory) and then they were asked if said stimuli induced frissons. For the tactile stimuli a device was used for massages in the head and a feather in the neck and for the gustative 2 acid juices were used.

Goldstein A. (1980) argues that the most frequent place of origin of the frissons is the upper area of the spine (67%), the back of the neck (62%), the shoulders and lower part of the spine dorsal and the scalp that were mentioned by 25% of the participants. In general, the propagation of tremors occurs with an upward radiation patterns; to the scalp (65%) and face (39%), out to the shoulders (61%) and to the arms (63%) and down to the spine (52%), to the chest (34%), to the genital region (29%), to the thighs (30%) and to the legs (28%).

Goldstein's study showed that the greatest ability to provoke frissons corresponded to musical passages (96%), movie scenes (92%), natural beauties or art (87%), physical contact with others people (78%) and nostalgic moments. With less frequency to provoke frissons were some moments of a sporting event (52%), some fragrances (39%), physical exercises (36%) and military parades (26%). He also showed that the frissons were invariably associated with sighs, palpitations, tension in the jaws and facial muscles and a lump in the throat and even a soft orgasm. As a summary, 91% of one of the two groups of participants and 76% of those in the second group found them pleasant.

Craig D. (2005), made an experiment consisting of making objective and subjective measurements to evaluate the physiological and psychological changes that occur during the frissons induced by music. The results confirmed that the frissons are associated with physiological and discrete events that can be measured objectively, both in musicians as in normal listeners and in front of known or unknown pieces of music. The results indicate that the frissons are associated to changes in the GSR and sometimes to a piloerection. The study concludes that frissons are more related to a general activation of the sympathetic branch of SNA than to thermal changes in skin temperature. According to Salimpoor V. et al (2009), the frissons are not experienced by anyone, but since the physiological parameters to evaluate them are so objective, the effectiveness of their occurrence is simple to determine, although not the degree of pleasure they provoke.

According to Harrison L. and Loui P. (2014), extreme emotional experiences (spikes), which include those that provoke musical frissons, occur in two distinct areas of the dopaminergic reward system (neurotransmitter present in areas of the brain that regulate pleasure and motivation). In the caudate nucleus that is activated anticipating the maximum of the emotion and in the nucleus accumbens that is activated immediately after the maximum. Additionally, the structural and functional connectivity between the auditory, emotional areas and the reward processing system is a successful predictor of the frissons.

Blood A. and Latorre R. (2001) found that music-induced frissons were associated with changes in blood flow in the midbrain, in the striatum, in the bilateral amygdala, in the left hippocampus, and in the cortex ventromedial prefrontal.

This pattern may reflect a "craving" effect, similar to that associated with sex, drugs and food. It is possible that the reason why the human being develops such an affinity for the frissons induced by music is that when we experience them we develop a dopaminergic anticipation by repeating the experience, with those who are slightly addicted to the musical stimuli that induce them.

According to the authors Salimpoor V. and Zatorre R. (2013), the dopaminergic system initially evolved to give the organism a sense of pleasure in order to reinforce adaptive behaviors. Later men learned to use other more powerful and efficient means of activation. Many synthetic drugs point to this system to release dopamine and thus produce states of euphoria; It is possible that an aesthetic stimulus such as music produces a similar effect.

Colver M. and El-Alayi A. (2015), highlight the emotional nature of the Frissons and argue that a greater openness to experiences, one of the five features of the personality model of the "Big Five" (together with responsibility, extroversion, kindness and neuroticism), would cause a greater number of frissons. To demonstrate this, they evaluated the features of a group of participants who were later made to listen to music known to induce frissons. The occurrence of these was verified by means of self-reports and the galvanic response of the skin and, as expected, the frequency of frissons was positively correlated with the degree of openness to the participants' experiences.

The results of this experiment by Colver and El-Alayi indicate that not only the emotions explain the frissons, but also that there are cognitive factors involved, this agrees with the findings of Grewe et al (2007), as to what was more likely that people who concentrate more on a particular music could experience more frissons. In addition, these researchers concluded that frissons have an important cognitive component associated with anticipation, prediction and working memory, all of which are related to the personality trait of openness to experiences.

Arrom M. (2015), conducted an experiment whose objective was to know how personality and coping strategies (adaptive and maladaptive) affect the perception of pain and the daily life of patients with chronic pain.

By coping strategies is called the set of cognitive and behavioral strategies that the person uses to manage internal or external demands that are perceived as excessive for the individual. The conclusions of the study were the following:

The coping strategies that least interfere in daily life are the adaptive ones; such as self-instructions, ignore pain and distracting responses.

The most adaptive personality trait is openness to experiences.

Visual Stimuli

More than 80% of human sensory impressions are perceived through our eyes and ears and therefore audiovisual stimuli, caused by rhythmic lights and sound stimuli, are a way of externally influencing the brain and an effective method to diminish the stress, anxiety and the perception of pain. It has been shown that the distraction caused by audiovisual stimuli diminishes pain as a result of distracting the attention from it.

The authors Bloomer C. et al (2014) point out that stressful events, where there are visual and/or auditory stimuli, provoke the "fight or flight" response that promotes the activation of the sympathetic nervous system and causes measurable physiological changes in the body. These authors made a study comparing the sympathetic response to stress caused by auditory stimulation (hearing aids and blindfolding) versus visual stimulation (videos). The authors defined as a response to stress a significant increase in heart and respiratory rates and the galvanic response of the skin.

As a result the heart rate decreased more for the visual stimuli than for the auditory ones, the conductance increased more for the visual ones and the respiratory frequency increased more with the auditory stimuli. The researchers concluded that there are no significant differences between auditory and visual stressors, although this could be explained by the characteristics of the video contort.

M M Tse et al (2002), argued that for hospitalized patients, and subjected to medical procedures, the environment causes anxiety, fear and depression, which aggravated the pain. The researchers evaluated the effect of visual therapeutic stimulation, through videos, on the threshold of pain and its level of tolerance to it.

To verify this hypothesis, the authors did a controlled trial in which the participants were divided into 2 groups, one of them was a video presented with landscapes, but in silence and the second one with a blank screen. The pain was caused by the modified tourniquet technique, the pain threshold was defined at the time the patient reported the start of the pain and the level of tolerance was defined as the moment the person reported unbearable pain. With the results obtained in the experiment, the authors concluded that visual stimuli considerably increased pain threshold and pain tolerance.

On the other hand, the authors Triberti S. et al (2014), highlight that pain is reduced by environmental stimuli that divert attention from harmful events so that immersion in a virtual reality environment, generated by computer technology, is an efficient tool of distraction in pain management.

In U.S. Pat. No. 6,425,764 B1, the inventors point out that during exposure to virtual reality therapy, patients receive visual, auditory and tactile sensory stimuli, with which they can interact. Virtual therapy is a non-invasive, three-dimensional, interactive, self-help and low-cost immersion experience. In this context, they developed a methodology to treat different psychological, psychiatric or medical conditions using a psychological strategy associated with a virtual reality environment.

The authors Shaygan et al (2017), point out that one of the main advances in the understanding of pain is that nociception is not identical to the perception of pain, since the former is influenced by various psychological factors. As an example, it has been shown that the level of attention and/or the emotional state regulate the response to pain. The emotional state is evaluated in two dimensions, valence and excitement, where the valence is defined as positive (pleasant) or negative (unpleasant), while the excitement (high or low) reflects how calm the person is.

These authors then carried out an experiment to investigate the attenuating effect of different images in patients with chronic pain, since they were interested in observing whether the attenuating effect of the pain was regulated by the valence of the photos and the excitation. Patients were presented with photographs of their loved ones, landscapes and others and were asked to rate the intensity of the pain and their sensory and affective experience, before and after seeing the images. As expected, the results showed that the photos of the loved ones had a high positive valence and reduced the pain more than other types of images.

Vibrotactil Massages

The American Massage Therapy Association (AMTA) describes massage as "a soft manipulation of soft tissues including taking them, causing movements and/or applying pressure", another definition of massage is that it is "a systematic tactile form and a kinesthetic stimulation".

According to the author Field T. (2017), moderate massage is one of the most effective known of alternative therapies.

The mechanism most commonly used to explain the therapeutic effects of massage to reduce pain is the aforementioned Theory of the Gate, which considers that pain stimulates the nerve fibers shorter, less myelinated (Aδ) and slower to bring the stimuli to the brain, in comparison with the pressure signals that are conveyed by myelinated fibers, long (Aα and Aβ) and fast, which block the arrival of the former.

On the other hand the authors Rios E. et al (2017) point out that self-massage is an active technique where participants use several instruments (massage balls and others), to apply pressure on soft tissues in an attempt to imitate the techniques manuals The literature discloses various techniques in which positive responses to certain stimuli are associated, a phenomenon controlled by the Central Nervous System.

There are different mechanisms that have been studied to determine the effects of massage therapies in the relief of chronic pain. As an example, researchers Chang Y. C. et al (2015) conducted an experiment with patients with chronic myofascial pain who underwent two treatments; one received physical therapy and self-massage and the second only self-massage. The latter group showed a significant decrease in pain and an increase in the threshold of chronic pain.

In U.S. Pat. No. 7,927,294 B2 a manual device capable of massaging and washing the hair or massaging it, delicately and effectively, by means of a brush or part of it, is disclosed. A large number of projections are arranged on the surface of a flexible plate of the body of the device, where the brush is located, so that the projections are symmetrical with respect to an axis A and perpendicular with respect to an axis D of in the surface of the body plate.

According to the authors Goldstein S. and Casanelia L (2010), the vibratory massages are groups of techniques that consist of rhythmic manipulations of the soft tissues. These rhythmic manipulations have a unique oscillation pattern that depends on the type of vibration applied and of the "seal" of the vibration (light and/or caressing, slow and/or heavy or rough). Vibrations that differ in frequency, amplitude, pressure and area of exposure cause resonances or repercussions, undulations and rebounds within the body.

In the utility model CN 205181749U a multifunctional vibrant physiotherapy equipment is described, which includes the body of the physiotherapy equipment, wherein the body of the physiotherapy equipment passes through a hinge connection, and which is equipped with a slot for massaging the feet.

Vibration is a mechanical stimulus characterized by an oscillatory wave. The biomechanical factors that determine its efficiency are frequency, amplitude, acceleration and duration. Three ways of administering this type of therapies are recognized:

The vibration enters the human body by the hand by grasping a vibrating element.

The vibration is applied directly to the muscle through a vibrating element.

The vibration enters the body through the feet on a vibrating platform.

Uher I. et al (2018), conclude that depending on their characteristics the vibration can affect the human body in different ways, such as changes in the elasticity of blood vessels, improvements in peripheral circulation, stimulation of lymphatic circulation, relief of pain, increase in the elasticity of tendons and fascia, increase in muscle strength and flexibility, improvements in the functioning of the metabolism and in mental health and relaxation in the whole organism.

Poenaru et al (2016) point out that the vibration stimulates specific receptors, cutaneous and musculo-tendinous. Afferent impulses travel through the spinal cord to the thalamus and to cortical regions. The local response to vibration is a tonic vibrational reflex, which depends on the frequency, amplitude and length of the tendons and muscles. In relation to the equipment to apply the vibration there are small units that are applied directly in a muscle or a tendon, to larger equipment where the patient receives them standing up; platforms. Currently there are two types of platforms in the market; those that produce alternate lateral vertical sinusoidal vibrations (SV) and those that produce vertical synchronous vibrations (VV).

In the patent DE 102010047757B3 a dumbbell is described with a tubular bar, inside which there is a vibrating device, which is characterized by having two electric motors, one at each end of the dumbbell, which are connected to each other by means of an axis that rotates.

In U.S. Pat. No. 5,327,886 is disclosed a device for electronic massage that has the function of a pad and includes an eccentric wheel driven by a motor that turns and produces vibration and a thermoelectric module that produces cold or heat for the pad, as appropriate. The device also has a fan to dissipate excessive heat and can be used only as a cold compress or as a compress and massager.

Boehme R. et al (2018) did a study to differentiate tactile stimuli (including massages and caresses), made by oneself from those of third parties, since the mechanism that causes this distinction is currently unknown. Through the results obtained in functional magnetic resonance Imaging (fMRI), these researchers concluded that touching oneself causes a broad deactivation in the brain, which clearly differentiates it from affective contact made by third parties. This difference was significant and was manifested early in the sensory processes by the amplitude of the spots in the right anterior cerebral cortex (less clear when touching Itself). At the behavioral level, sensory attenuation produces a higher perceptual threshold in these circumstances, that is, the stimuli themselves are perceived less.

The fact of having a lower perception to the tactile stimuli provoked by oneself when compared with those of third parties, could have certain similarity with the fact that we cannot tickle ourselves. Although according to the authors Blakemore S. et al (2000), the attenuation mechanism in tickling is due to sensory predictions made by a model of internal anticipation in the motor system. The anticipation model can predict the sensory consequences of the movement, anticipating the command to be executed, which means that when the movement occurs by will, its sensory consequences have already been predicted in advance.

According to Harvey L. (1992), all models of stimulus detection and discrimination have at least two psychological components or processes; the sensory process (which transforms physical stimulation into internal sensations) and the decision process (which decides the response to adopt). All this can be summarized in the following sequence, where the detection is based on the two internal processes (sensory and decision):

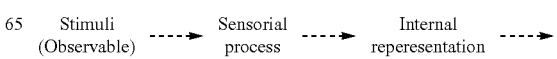

-continued

In a study conducted by Sutton S. et al (1965): it was observed that the evoked potential by light and sound stimuli in conditions of uncertainty showed differences, when compared with the sensory modality, depending on the level of subjectivity of the individual in the presentation of the stimulus (perceptions, arguments and language based on the point of view of the subject). There were also differences in the evoked potential according to whether the modality in the presentation of the stimulus was correctly anticipated by the individual.

Cold Therapy

According to the author Rastogi A. (2018), cold therapy or cryotherapy is the treatment for pain that uses the method of locally cooling the irritated nerve and is used for rehabilitation with a mild cold (inflammation, edema and others) or to destroy with intense cold tissues malignant or not. Cryotherapy includes many specific techniques; ice bags, frozen gels, Ice massages, immersion in ice coolants (eg N2) and others.

Ernst E. and Fialka V. (1994), maintain that the body or its parts can be easily cooled by ice or other means and that this causes a decrease in the temperature of the skin, of the subcutaneous tissues and to a lesser extent of the deeper muscle tissues, bones and joints. The kinetics of the change in temperature depends, among other factors, on the absolute temperature of the cooling agent, on the duration of the application time, on the vascularization of the tissue and on the local flow of blood. Generally the cooling effect is of short duration once the cooling agent has been removed, but in the deeper tissues the cold may take longer to dissipate.

Chesterton L. et al (2002), affirm that several studies have been conducted to establish the critical level of cooing of different types of tissues to obtain specific effects. As an example to achieve a localized analgesia in the skin a temperature below 13.6° C. is required, to reduce the conduction velocity of the nerves by 10%, a temperature lower than 12.5° C. is required and to reduce the enzymatic activity by 50%, temperatures below 10 or 11° C. are suggested.

The authors Smith K. and Zhu L. (2010) developed a model of the human torso to simulate the behavior of the spinal cord before it cold, where the torso is modeled as a rectangular column and the spinal column and spinal cord as tubes concentric separated by the cerebrospinal fluid. The spine, composed of cartilage and bones, is simplified as a homogeneous cylinder, the spinal cord as a whole in which the gray matter is not distinguished from the white and the rest of the torso is modeled as muscle tissue. The model assumes all the thermal properties as homogeneous and isotropic and the Pennes heat transfer bio equation is used.

Eckart S. (1974) argues that tremors called chills are a suitable somatomotor response for thermal stress caused by cold. He also states that several researchers observed tremors induced by the cold during the cooling of the spinal cord, which were verified by visual and palpatory controls and agreed that they are real chills caused by a cold stimulus in the spinal cord.

On the other hand there are experiments with anesthetized dogs showing that chills induced by a) external cooling, b) hypothermia and c) by a selective cooling of the spinal cord, caused tremors of equal frequency in animals. Then it was observed that those irruption called chills, or "frisson reflexes", could be observed at the beginning of the tremors in the 3 types of cold stimulation mentioned above.

U.S. Pat. No. 6,023,932 A1 shows a portable device for the local transfer of cold in humans and animals when they require it to relieve pain or inflammation of both muscles and joints. The device comprises a thermoelectric unit having a cold side and a hot side, a DC power source connected to the thermoelectric unit, a heat sink that is associated with the hot side of the thermoelectric unit, a fan to reduce the heat of the heatsink and a band or the like to fix the device to the person.

In the US patent 2007/0225781 A1, an apparatus and method is described and/or cooling or heating certain areas within the body. With respect to the cold the system can cool the nerves of the body up to about 15° C., which decreases nerve impulses. The system has cold elements that can be Peltier cells or a catheter through which cold or hot water is passed through. The hot portion of the Peltier cells can be cooled by a coolant that absorbs the heat and then dissipates it.

Aromatherapy

According to Edris A. (2007), essential oils are natural compounds, complex and with different components, mainly terpenes, and there are different ways to extract them from different plants, including water or steam distillation, extraction with solvents, with pressure or with fluids. supercritical Essential oils have been attributed different beneficial properties, which according to the author has been scientifically proven. More than 40 plant derivatives have been Identified for medicinal or therapeutic use, where lavender, *eucalyptus* and chamomile are the most used.

Louis M. and Kovalsky S. (2002) conducted a study to measure the response of 17 hospitalized cancer patients to a lavender oil aromatherapy humidifier. The vital signs were measured as well as anxiety, depression and the feeling of well-being. The results showed a positive but small effect on blood pressure, pain, anxiety, depression and level of well-being.

Lakhan S. et al (2016) point out that there are many studies in which the benefits of aromatherapy are exposed, however research has focused on the management of depression, anxiety, muscle tension, sleep, nausea and the pain. For this reason they did a literature review and a meta-analysis to demonstrate the effectiveness of aromatherapy in the treatment of pain, selecting 12 of those studies. The results indicated that there Is a positive effect of aromatherapy, compared to a placebo or conventional treatments to reduce pain. A second analysis found that aromatherapy is more consistent to treat nociceptive and acute pain than inflammatory and chronic pain, respectively. These researchers conclude that aromatherapy is safe, that no negative effects are reported, that the costs of treatments are low and that more research is required to fully understand the clinical applications.

On the other hand, Schneider R. et al (2018), like Lakhan et al (2016), affirm that there are few studies regarding the efficiency of aromatherapy and that some have weaknesses in research methodologies. In their work they analyze the conditions under which aromatherapy is more efficient, for which they studied the characteristics of the olfactory system and the characteristics that odorants must have to have therapeutic effects. Then they tested the effect of an inhaler (AromaStick), which acts on various physiological systems, such as cardiovascular, endocrine pain and others, both in the long and short term. The authors conclude that the inhalation of essential oils had an immediate, important and clinically relevant result as long as they were delivered in a high concentration and by an appropriate device.

International patent application WO 2006/084921 A1 discloses a diffuser for volatile substances of the type that are connected to the electrical network, for sequentially or simultaneously diffusing several fragrances by manual activation or according to a predetermined program. In the U.S. Pat. No. 9,849,206 B1 a diffuser of liquid perfumes is described, which allows the release of these to the environment only when desired, in order to prolong its use with the consequent saving of perfume.

Perceptual Learning

Gold J. and Watanabe T. (2010), point out that perceptual learning is the increase, fruit of experience, of our ability to understand what we see, what we hear, what we feel like or smell. These changes are permanent or semi-permanent, so they differ from short-term mechanisms such as sensory adaptations or habituation. Permanent or semi-permanent changes have been taken as evidence of the plasticity of brain regions involved in sensory tasks.

Changes in sensory tasks are not merely incidental but rather adaptive and therefore provide various benefits such as greater sensitivity to pick up weak or ambiguous stimuli or require a lower level of stimulus or a shorter period of time to perceive them. In summary, perceptual learning has three characteristics; it is a lasting learning, it is perceptual (the way the brain senses sensations) and it is a product of practice (experience).

The ways in which perception adapts to tasks and the environment are the following: differentiation, unification, attentional weighting and impression of stimulus.

a) Differentiation: One of the most used mechanisms for perception to adapt to the environment is when the percept (object of perception) differs from the rest. The stimuli that were indistinguishable now separate.
   b) Unification: It is the mechanism of perceptual learning that goes in the opposite direction of differentiation. Unification involves the construction of singular units in response to complex configurations. By unification a task that could require the detection of several parts now only needs one.
   c) Attention weighting: When by practice or experience people increase their attention to the perceptual dimensions and characteristics that are important and reduce attention to the dimensions and characteristics of minor importance.
   d) Impression of the stimulus: A second way in which perception can adapt to the environment is by marking them. By marking them, the detectors (receivers) specialize in stimuli or parts of stimuli.

Synchronization of the Senses

According to Recanzone G. (2009) objects and events in real life comprise multiple sensory attributes, which are processed in different independent modes. However, the way to combine this sensory information to give shape to a unique perceptible object is not yet clear. Combining information about a common source with different characteristics, through the senses can improve discrimination and reaction to various objects.

King A. (2005) argues that there are numerous neuronal and non-neuronal factors that Influence how long the signals, which arise from the same source, reach the multisensory neurons in the brain. As an example, sound travels much slower than light and therefore arrives later, however the process of auditory transduction is much faster than the process of transduction in the retina, which makes a difference in the response of both neurons, auditory and visual, from 40 to 50 milliseconds in favor of the latter.

This author affirms that synchronization over time is a particularly powerful tool to unite stimuli and it has been demonstrated that humans are capable of performing an accurate assessment of the simultaneous occurrence of auditory and visual cues, despite variations in relative times in that are slow to arrive. A second powerful tool to unify stimuli is the spatial one, since there are multiple cases in which a sensory modality dominates the percept of an object or multisensory event. A classic example is the ventriloquistic effect, where the percept of an auditory stimulus is "captured" by the spatial location of a visual stimulus.

According to Noy D. et al (2017), even though the signals of the different sensory systems are processed with noise and asynchronously, the function of the Central Nervous System is to make the best estimate from inaccurate information; what it would do through a mechanism that operates as a Maximum Likelihood Estimator. The efficiency of this operative function can be seen when two people walk together, for which both individuals must synchronize the signals of movement, of touch, visual and auditory with those of their own signals.

GENERAL DESCRIPTION OF THE INVENTION

Chronic pain has a physical, emotional and cognitive dimension in the individual and the frissons are positively related to all of them with the aim of alleviating the chronic pain of patients. The purpose of this invention is to induce frissons through multisensory and multimodal stimulation, wherein the stimuli that elicit them are related to the senses of hearing, vision, touch, and smell. To achieve this objective, it is important that the various stimuli act synchronously around the music, since the latter has proven to be the most efficient way to elicit them. A secondary objective of the present invention is to intensify and keep the previously induced frissons in time in order to maximize the pain relief in the patient.

It should be noted that taste was not considered within the methodology used, since taste and smell have the same type of receptors and both are stimulated by the molecules that float in the air. Odorants come from molecules in the air that stimulate the receptors in the olfactory bulb; if there is no receiver for that specific odorant, the odorant has no smell. If one of the those senses does not work well, the other will not work either because of the relationship between the receptors. There is also a practical reason derived from the lack of literature, with the exception of the work of Grewe O. et al (2010), in relation to the effect that gustatory stimuli have on inducing frissons.

In general terms, the equipment for the treatment of chronic pain of this invention, which can be operated by the patient himself or initially with the help of an assistant, comprises a computer with a music and a video player and a computer system that mainly controls the hydraulic circuit with a cooler and an actuator, illumination and a diffuser, and to enhance their effects, recourse to perceptual learning. Below are the mechanisms, considerations and limitations to elicit such stimuli and the expected responses, frissons and others, for each one of them.

Musical and Visual Stimuli

It has been demonstrated that music and visual stimuli can produce intense emotions and frissons, as well as improvements in physical condition, a decrease in stress and anxiety, depression reduction, improvements in mood and cognitive functions, and a decrease in chronic pain. Notwithstanding the above, not all musical and visual stimuli are appropriate to elicit frissons and decreases in pain. Next, different aspects of the patient, the stimuli and the way to present them are analyzed.

Musical Stimuli

Regarding music, we must bear in mind the characteristics of the patient (sex, age, behavior, emotions, feelings and mood), about of his illness, physical state and others), of the physiological parameters (blood pressure, heart and respiratory rate), conductance of the skin and others), of the emotions that the music induces (joy, anxiety, sadness and others), about the characteristics of the music (musical genre, volume, rhythm, harmony, metric, compass, melody and the notes), the surrounding environment (luminosity, noise, temperature, colors and others), the frequency of stimuli presentation and duration of sessions, preferences for self-selection or delivery, sequence and randomness.

Physiological and Psychological Effects of Music

Emotions, whose understanding and effects are fundamental in this invention are defined as a complex state of feelings that result in physical and physiological changes that influence on thoughts and behavior: emotionality is associated with different psychological constructs including temperament, personality, mood and motivation. There is a debate about the emotions that music elicit in individuals, Arjmand H. et al (2017) and others sustain that they respond to significant environmental events potentially important for the survival of the individual (utilitarian model, reaction fight-flight). However, other studies show that music elicit emotional aesthetic reactions that go beyond the merely utilitarian.

The generation of an emotion in the subcortical regions of the brain activates the hypothalamus, the Autonomic Nervous System (ANS) and the release of adrenaline and cortisol. The activation of the ANS includes the sympathetic nervous system, which prepares the warming and strength reactions (fight-flight) and the parasympathetic one that acts during the digestion and the rest, both systems predominate according to the context. The sympathetic causes, through hormones, the alteration of different tissues and organs, including cardiac and respiratory activity, as well as blood pressure. According to Koelsch S. and Jancke L. (2015), the heart rate (HR) and respiratory rate (RF) increase in response to the exciting music (stress) and decrease with the relaxing music. During the musical frissons (involving shuddering and piloerection) the FC and the FR increase. In addition both of them tend to increase with the music, when compared with silence and FC decreases with the unpleasant music and increases with the pleasant one.

Plutchik R. (1980) developed an evolutionary theory about emotions and proposed that humans have evolved to adapt our organism to the environment and divided emotions into 8 categories, with emphasis on those related to survival: fear, surprise, anger and 8 more of an advanced level. The rest of emotions would be combinations of the previous ones to broaden the range of experiences. According to this theory, emotions vary in their degree of intensity and the more intense the emotion more will motivate the related behavior.

On the other hand, feelings are moods that are produced by causes that impress you, and these can be cheerful and happy or painful and sad. The feeling arises as a result of an emotion that allows the subject to be aware of his mood. Unlike emotions, states of mood (AE) do not have a clear event that causes them, or if it had occurred, it is not clearly Identifiable by those who experience it. AE are diffused and longer lasting affective states that do not have an specific orientation towards a certain stimulus"; Fridja N. (1999).

According to Turk D. and Wilson H. (2010), the evidence from several studies supports the role of biological, psychological and environmental factors in the etiology, exacerbation and maintenance of chronic pain. It is common for this type of patients to experience anxiety and fear and a low state of mind, which worsens their situation.

Anxiety: There are studies that show that anxiety levels can predict the severity and behavior of patients with chronic and acute pain. As well as that the techniques of reducing anxiety and the use of anxiolytic drugs reduce the pain derived from medical procedures.

Fear: There is scientific evidence that negative individual evaluations of pain, including pessimistic interpretations of it, such as that the belief that pain is associated with various pathologies, and that therefore harms, contribute to the development of pain-fear association. The extremely negative interpretation of pain induces fear responses; physiological (activation), cognitive and behavioral (avoidance).

Cognition: Cognitive changes that occur during fear increase the perception of the threat, increase attention, which then increases the catastrophic assessment of pain, avoidance and the level of disability.

Depression: It has been observed the existence of a considerable overlap between pain and depression which induces changes in the patient's neuroplasticity and brain neurobiological mechanisms. Such changes are fundamental to facilitate the occurrence and development of chronic pain and chronic pain induced by depression.

Below are described some characteristics of the person and about musical keys that can make the perception of music, emotions and moods differ between people.

Gender Identity: It has been suggested that if the information conveyed by a music has gender identity, related to a specific sex, the perception of the listeners would be slightly different. However there are opinions that music would not be related to gender characteristics, but would be attributed by listeners. Sergeant D. (2016).

Personality and mood: It was observed in a group of individuals who evaluated 50 musical pieces, in terms of the emotion they perceived (fear, happiness and others) that the evaluation done was a function of their moods. It was also observed that the personality of the individuals, measured prior to the evaluation, was linked to their evaluations Vuoskoski J. and Eerola T. (2011).

Rhythm and Tempo: The rhythm is the harmonious combination of sounds, voices or words, which include pauses, silences and cuts and the tempo corresponds to the speed with which a piece of music is played. The tempo determines the music causes happiness or sadness; a high tempo would be fun or expressive and a low one relaxing or boring. It has been observed that the tempo is the musical characteristic most related to the affective states. As for the effect of the rhythm, it would go in the same sense as the tempo. Fernandez-Sotos et al (2016).

Musical genre: The musical genre is a category that brings together musical compositions that share different criteria of affinity, such as its function, its instrumentation, its rhythm, its cultural characteristics and others. It has been observed that emotions, especially those related to valence, would be different depending on the musical genre. As an example, the opera involves music and singing as well as a large audio-visual framework from the orchestra and set design. Rodica F. et al (2011).

Visual Stimuli

Ulrich R. S. et al (1991), argues that the parasympathetic is involved in the recovery of normal levels of heart rate post-stress, since participants undergoing a stressful event recovered quickly after showing them a video with natural environments, this is consistent with a response of the vagus nerve, which is related to the parasympathetic and that (among its functions controls the heart rate). Gladwell V. et al (2012) showed that the parasympathetic activity of a participant group, after a stress, was greater when they observed a forest than a group of buildings and it was even greater when the forest was presented before the event stressful De Kort Y. et al (2006), performed an experiment in which the participants, after having done a stressful task, watched a film of nature, either on a small or a large screen, while evaluating their physiological parameters. The results indicated that the larger size of the screen and therefore the higher the degree of immersion in the film facilitated post-stress recovery in terms of physiological measurements.

Lee J. et al (2011), developed a study that supports the evidence that entering a forest serves as a natural therapy and investigates the physiological benefits of this practice. The results indicated that the environment of the forest significantly increased parasympathetic activity and reduces sympathetic activity among the participants (reduction of salivary cortisol), which contrasted with the results observed in an environment with buildings. Also in the psychometric tests, the fact of entering a forest improved the positive feelings and diminished the negative, when comparing the effect that there was in urban environments.

Banos R. et al (2012), did a work in which they tested two virtual environments in the elderly to see if they improved the mood, enjoyment and relaxation between them. The virtual environments contained exercises to generate autobiographies, mindfulness and quieting the breath. The results indicated that the presentation of both virtual environments increased enjoyment and relaxation while reducing the heaviness and anxiety.

For Grinde B. and Grindal G. (2009), contact with nature has beneficial psychological benefits by reducing stress, improving attention, having a positive effect on mental recovery and addressing attentional deficits. Additionally, there would be direct health benefits such as increasing longevity and Improving overall health. These benefits are associated with different natural experiences, such as natural deserts, parks and neighboring outdoor gardens. Additionally, several studies show the benefits of having plants indoors; in patients who have been shown photographs of hospital rooms, with and without indoor plants, the former reduce the stress reported in self-reports.

Diette G. et al (2003), did a study, presenting visual and auditory stimuli, to determine which visual distractors and sounds would reduce pain and anxiety in post-surgery patients, for which they presented murals with natural views, during and after of the procedure. They also received audio, before, during and after the surgery, at the same time as the intensity of the pain and the level of anxiety were evaluated. The results indicate an efficient response of distraction therapy with natural views and sounds to decrease pain.

Tactile Stimuli

In the present invention the tactile stimuli are presented by means of a closed hydraulic circuit with 3 pumps, one of them peristaltic 2 diaphragm, in addition to flexible tubes to drive the fluid, connections, an actuator, a cooler with Peltier plates, a sensor of temperature and a thermostat. This equipment allows to massage with light strokes and caresses, apply cold and vibrations, joint or combined, on the skin surface and the muscles of the upper part of the spine, of the patients.

The skin is innervated by skin receptors that belong to the somatosensory system, which make up the sense of touch and capture different specific stimuli that provide information to the Central Nervous System (CNS): mechanoreceptors, thermoreceptors (temperature) and nociceptors (pain). Where the mechanoreceptors provide information about touch, pressure, vibration and skin tension and according to their function are classified in the corpuscles of Meissner, Pacinianos and Ruffini and Merkel discs. Within the tactile receptors are tactile CT nerve fibers that have a low threshold, are not myelinated and have a low speed of signal conduction.

Ettzi R. et al (2018), affirm that caresses represent one of the most common ways to receive and transmit affections through touch and the evidence suggests that the pleasant perception of soft caresses is mediated by the tactile or tactile nerve fibers. CTs. To demonstrate this, the authors set up an experiment to observe how the physiological excitation varied according to the type of tactile stimulation applied to the forearm. During 9 to 60 seconds they applied slow (3 cms/s) or fast (30 cms/s) strokes and fixed or random tapping. The results indicated that slow caresses induced greater galvanic responses of the skin, in the subjective evaluations of the participants, than the patting.

According to Malamud-Kessler C. et al (2014), vibro-tactile perception depends mainly on the mechanoreceptors of rapid adaptation (Pacini and Meissnner corpuscles) and slow (Merkel discs). From the mechanical point of view, the sinusoidal wave has different characteristics (amplitude and firing frequency) that generate different vibrotactile perceptions. In addition, the vibration threshold is defined as the lowest oscillatory displacement capable of being detected and there are significant differences in the thresholds depending on the frequency, the magnitude, the contact area and the location of the vibrotactile stimulation.

The vibratory sensitivity in the corporal periphery has different characteristics depending on the body region that receives the stimulus, among them the existence of glabrous skin areas and the different receptors and afferent fibers that innervate them. The average density of the hair follicles in the forehead is significantly higher than in other areas of the body (292 hair follicles/cm2) compared to the back (29 follicles/cm2). Seah S. and Griffin M. (2006), compare the vibrotactile thresholds of men and women and of young people with adults (in glabrous and hairy skins) where it was possible to determine that the vibrotactile threshold for mature men and women in the mean finger, in thresholds of 31.5 Hz and 125 Hz, was 0.12 and 0.29 respectively for women and 0.14 and 0.23 respectively for men.

In order to provoke caresses in the present invention, vibrations, caresses and tappings are used, in addition to cold. Cutaneous thermosensation Is regulated by receptors that transduce, encode and transmit thermal Information. Park B. and Kim S. (2013) state that there are two types of thermosensitive fibers, some that respond to heat and others to cold.

Cold receptors, which perceive changes in skin temperature from 1° C., ranging from 15 to 30° C., are classified Into 2 groups, the superficial and the deep, of which 60% It's located in the periphery of the body. These receptors can transmit information through small fibers that are myelinated at a speed that goes from 5 to 15 m/s and also through C fibers.

According to Smith K. and Zhu L., previously cited, based on the physical and physiological parameters of their model, they conclude that a simple pad with a temperature of 20° C. for 30 minutes could lower the temperature of the spinal cord in more than 2.7° C. In 30 minutes and that the low temperature could be more than double if the temperature was reduced to 0° C.

In this invention the cold stimulus is applied by means of a low flow T.degree. that recirculates inside a tube of cross section of the hydraulic circuit and that Is applied on the skin and the muscles that cover the upper part of the patient's spine and in where the tube that touches the skin runs parallel to said column. The turbulence of the flow is mainly due to the work of the peristaltic pump and the passage of the flow through the actuator. The cold is obtained from a Peltier plate cooler. In this respect it's necessary to model the behavior of the turbulent flow caused by the peristaltic pump and by the actuator, however it is important to note that there are few analytical studies that treat them (if they exist are for steel tubes and hoses), as well as the transfer of heat between the fluid and the body tissues. Here are some models that explain these phenomena:

a) Three-dimensional behavior of tubes with expandable walls that transport compressible or non-compressible fluids. Gay-Balmaz F. and Putkaradze V. (2018) present a theory to explain them and that can be summarized in the following equations:

$$\begin{cases} \partial_t(\xi u) + \partial_s(\xi u^2 + pA) = p\partial_s A \\ a\ddot{R} - \partial_s \frac{\partial F}{\partial R'} + \frac{\partial F}{\partial R} = 2\pi R(p - p_{ext}) \end{cases},$$

Along with the conservation of mass and entrophy.

$$\partial_t \xi + \partial_s(\xi u) = 0, \partial_t S + u \partial_s S = 0,$$

b) Characteristics of turbulent flows; Turbulent flows have the following properties: Irregularity, three-dimensionality, diffusivity, dissipation and a high Reynolds number.

The equations of fluid mechanics are based on the fact that the dynamic behavior of a fluid is governed by the following conservation equations:
  The conservation of the mass or continuity equation.
  The conservation of the kinetic moment or the amount of movement.
  The conservation of energy.

By grouping the equations of conservation of the mass, the amount of movement and the conservation of energy, the Reynolds-Navier-Stokes equations can be obtained in three dimensions, according to Reynolds. (1895), which represents a system of 5 variables to be determined, but with 7 independent unknown identities. Although this is the most complete turbulence model, a general solution for this type of equations is not available and simpler models such as k-ε (k-epsilon) or kω (k-omega) are used. They are deduced from the LES (Large Eddy simulation) model, but they have restrictions.

b.1 Model k-ε (k-epsilon) of Hanjalic K and Launder B. (1972), is the most used model in computational fluid dynamics. It is a model of 2 transport equations to represent the turbulent properties of a flow. The first variable of this model is the turbulent kinetic energy (K), this variable determines the turbulent intensity, while the second variable represents the turbulent dissipation (Epsilon). This model is appropriate for totally turbulent flows and the equations are:
Turbulent Kinetic Energy:

$$\frac{\partial}{\partial t}(\rho k) + \frac{\partial}{\partial x_i}(\rho k u_i)\frac{\partial}{\partial x_j}\left[\left(\mu + \frac{\mu_t}{\sigma_k}\right)\frac{\partial k}{\partial x_j}\right] + G_k + G_b - \rho_\epsilon - Y_M + S_k$$

Turbulent Disipation:

$$\frac{\partial}{\partial t}(\rho \epsilon) + \frac{\partial}{\partial x_i}(\rho \epsilon u_i) =$$

$$\frac{\partial}{\partial x_i}\left[\left(\mu + \frac{\mu_t}{\sigma_\epsilon}\right)\frac{\partial \epsilon}{\partial x_i}\right] + C_{1\epsilon}\frac{\epsilon}{k}(G_k + C_{3\epsilon}G_b) - C_{2\epsilon}\rho\frac{\epsilon^2}{k} + S_\epsilon$$

b.2 Model k-ω (k-omega) of Wilcox D.C. (2006)
The turbulent viscosity Vt, as required in the RANS equations (Reynolds Averaged Navier-Stokes) is given by: VT=k/ω, while the evolution of k and .psi. is modeled as:

$$\frac{\partial(\rho k)}{\partial t} + \frac{\partial(\rho u_j k)}{\partial x_j} = \rho P - \beta^* \rho \omega k + \frac{\partial}{\partial x_j}\left[\left(\mu + \sigma_k \frac{\rho k}{\omega}\right)\frac{\partial k}{\partial x_j}\right],$$

$$\text{with } P = \tau_{ij}\frac{\partial u_i}{\partial x_j},$$

$$\frac{\partial(\rho \omega)}{\partial t} + \frac{\partial(\rho u_j \omega)}{\partial x_j} =$$

$$\frac{\gamma \omega}{k}P - \beta\rho\omega^3 + \frac{\partial}{\partial x_j}\left[\left(\mu + \sigma_\omega \frac{\rho k}{\omega}\right)\frac{\partial \omega}{\partial x_j}\right] + \frac{\rho \sigma_d}{\omega}\frac{\partial k}{\partial x_j}\frac{\partial \omega}{\partial x_j}.$$

The RANS equations and the nomenclature of the k-ε (k-epsilon) or the k-ω (k-omega) models are not presented, since they can be seen in several references.

Peristaltic Pump, Turbulent Fluid and Vibration

As mentioned earlier in this Invention, the turbulent flow that causes the vibration and stimulation of the skin and the muscles that cover the spine is caused by the narrowing of the flow by the actuator or by the peristaltic pump.

According to Takabatake S. et al (1988). the pumping of a peristaltic pump is a function of four parameters: the radius φ, the number of waves a, the number of Reynolds Re and the time of flow (without dimension) ȳ. There are different definitions for the Reynolds number, however in a paper done by Cheng X. et al (2017) they use the following equation:

$$Re = \frac{\rho \times V \times D}{M}$$

Where ρ Is the density of the fluid (kg/m3), v is the average velocity of the fluid. D is the diameter of the tube (Internal diameter if circular, in mtrs) and μ is the dynamic viscosity of the fluid (Pa×s=N×s/m2=kg/(m/s) As an example and from this equation, calculate the behavior of the Reynolds number, for different diameters and velocities of the peristaltic pump, with values: p=1.08 kg/m3 and the inner diameter of the tube is 1.55×10↑−3. The viscosity of the fluid was estimated at 1.06×10↑−3 Paxs.

The Reynolds number for pump speeds of 100 rad/min, at a flow velocity of 1.69 m/s was 2678.22 and from that pump speed they were Increasing from 10 to 10 radians/min until reaching a maximum of 190 radians, with a flow velocity of 3.17 m/s and a Reynolds number of 5014.69. When the speed of the pump exceeded 160 radians/min, the Reynolds number was greater than 4000, considered as turbulent (since Re<2300 is a laminar flow, with 2300<Re<4000 is a transient flow and greater than 4000 turbulent). In short for the purposes of this invention, the greater the number of Reynolds, the greater the fluid turbulence and the greater the vibration of the tubes and the tappings that stimulate the cutaneous surface covering the patient's spine.

Heat Transfer from Tissues to the Hydraulic System

An Important element to be determined in this invention is the heat transfer between the cutaneous, muscular and bony tissues, from the upper part of the spine and the cold and turbulent fluid (Reynolds N), contained in a tube parallel to the first ones and whose characteristics are to be straight, of circular cross section, of smooth inner surface and that transport an Incompressible fluid.

According to Subramian R. (2014), the Ditus-Boelter correlation is the most recent way, and the most generally used for fluids with Prandtl number in the range of 0.7 to 100 and in tubes with L/D>60, where L is the length and D the diameter of the tube. This correlation is simple to apply but is not accurate when the temperature differences between fluids (cold, heat) are very high and the Internal surfaces of the tube aren't smooth. The Nusselt No (Nu) is the ratio of heat transmission by convection and conduction, in a delimited flow.

| Correlation | Constraints |
| --- | --- |
| $Nu_{Dh} = 0.023\ Re_{Dh}^{0.8}\ Pr^{0.4}$ where: | $0.6 \leq Pr \leq 160$ $Re_{Dh} > 10000$ |
| Dh is the hydraulic diameter [m] Re is the Reynolds number [–] | $\frac{L}{D} > 10$ |
| Pr is the Prandtl number [–] Nu is the Nusselt number [–] | |

The Prandtl No. can be represented as the relationship between the kinematic viscosity and the thermal diffusivity of a fluid $\alpha$ (v/$\alpha$). The Ditus-Boelter correlation should be used in flows with a Reynolds number not higher than 10,000 but in practice it is used with values lower than that.

Hydraulic Actuator Mechanism

A second source of turbulences within the hydraulic circuit of the present invention, are those coming from a hydraulic actuator, which causes vibrations in the walls of the tubes of the first, which are transmitted to the skin and muscles that cover the upper part of the spine.

Moreover the hydraulic actuator consists of a cylinder that moves longitudinally and in both directions, on a pair of pistons that are fixed and are hollow; water circulates inside of them, and that end in ringed nozzles that point in an opposite way, towards both directions of the cylinder, discharging into the tubes of the circuit and where the actuator is fed alternately by water driven by each one of the two ways solenoid valves, two steps, located on the sides of the cylinder and whose openes is controlled by a computer system.

The flow continuity equation, which describes the behavior of a permanent, Incomprehensible and unidimensional flow like that of the water Inside the pistons. Is the following:

as the water Is practically incompressible $\rho 1 = \rho 2$ remains;

$$\rho 1 \times V1 \times A1 = \rho 1 \times V2 \times A2$$

the inlet flow Is equal to the outflow (from the nozzle).

$$Q = V1 \times A1 = V2 \times A2$$

Since the flow inside the pistons is laminar, the following equation can be used to determine its speed:

$$v = v_{(max)}\left[1 - \left(\frac{r}{R}\right)^2\right]$$

Where R=tube radius and v (max) Is the maximum velocity at the center of the speed profile, which Implies that towards the exit of the nozzles the fluid speed Increases. Shademan Y. et al (2012) made an investigation to study the effect of the geometry of four nozzles with an Incompressible fluid and they observed that locating a ring in the vicinity of the outlet of a nozzle Increases the Incidence of turbulence and flow speed.

Model for the Release and Intensity of the Smell of a Fragrance

To model the release of fragrances from a simplified matrix, used in the formulation of different flavored products, the authors Costa P. et al (2015) used a new model that, depending on the conditions, could be used in this invention. Henrys law, for a chemical dissolved in a liquid, is defined as the ratio of the equilibrium relations between the gas and liquid phases, at a given temperature.

$$Ci(gas) = H \times Ci(líquido),$$

where H Is the component of Henrys law for H and Ci (gas) and Ci (liquid) are the concentrations of the component of the fragrance I in the gas and in the liquid phase in (gr/L).

The literature shows that the olfactory perception of a mixture of fragrances can be calculated from a combination of variables, the concentrations of odorants in a gas, its chemical structure, the odor threshold and the neuronal signals in the transduction.

This model simplifies the analysis to predict a) the Intensity of the smell and b) the character of a mixture of fragrances and the concentration of the vapors in It, using a psychophysical model known as the Law of Steven's Psychophysics, which relates the magnitude of the sensation and Intensity of a stimulus and the Strongest Component Model.

The intensity of the smell perceived in a mixture of fragrances was calculated from the concentrations used in the Stevens Law. The model is derived from sensory experiments related to the relationship between the magnitude of the applied stimulus and the perceived sensations and contemplates non-linear relationships between both and for the related to smell can be expressed assuming that the perceived sensation ($\Psi$) is proportional to the magnitude of the stimulus (Ci gas) raised to an exponent ni:

$$\psi_1 = \left(\frac{C_i^{gas}}{ODT_T}\right)^{n_i}$$

Where Ci gas is the concentration of the odorant in the gas phase, ODTi is the threshold for the concentration of odor in the air (units of mass or moles per volume) and the parameter ni is defined as the exponent of the Law of Stevens for each odorant in particular.

FIGURES

FIG. 1 (1A and 1B) shows a patient in a therapy session to alleviate chronic pain by inducing, intensifying and maintaining their own frissons, by presenting multisensory and multimodal stimuli. Musical, visual, tactile and olfactory and that are elicit by actuators of a workstation with a PC and a monitor, an operating system, a multimedia program, an hydraulic circuit and an actuator controlled by a computer program.

Figure 4:
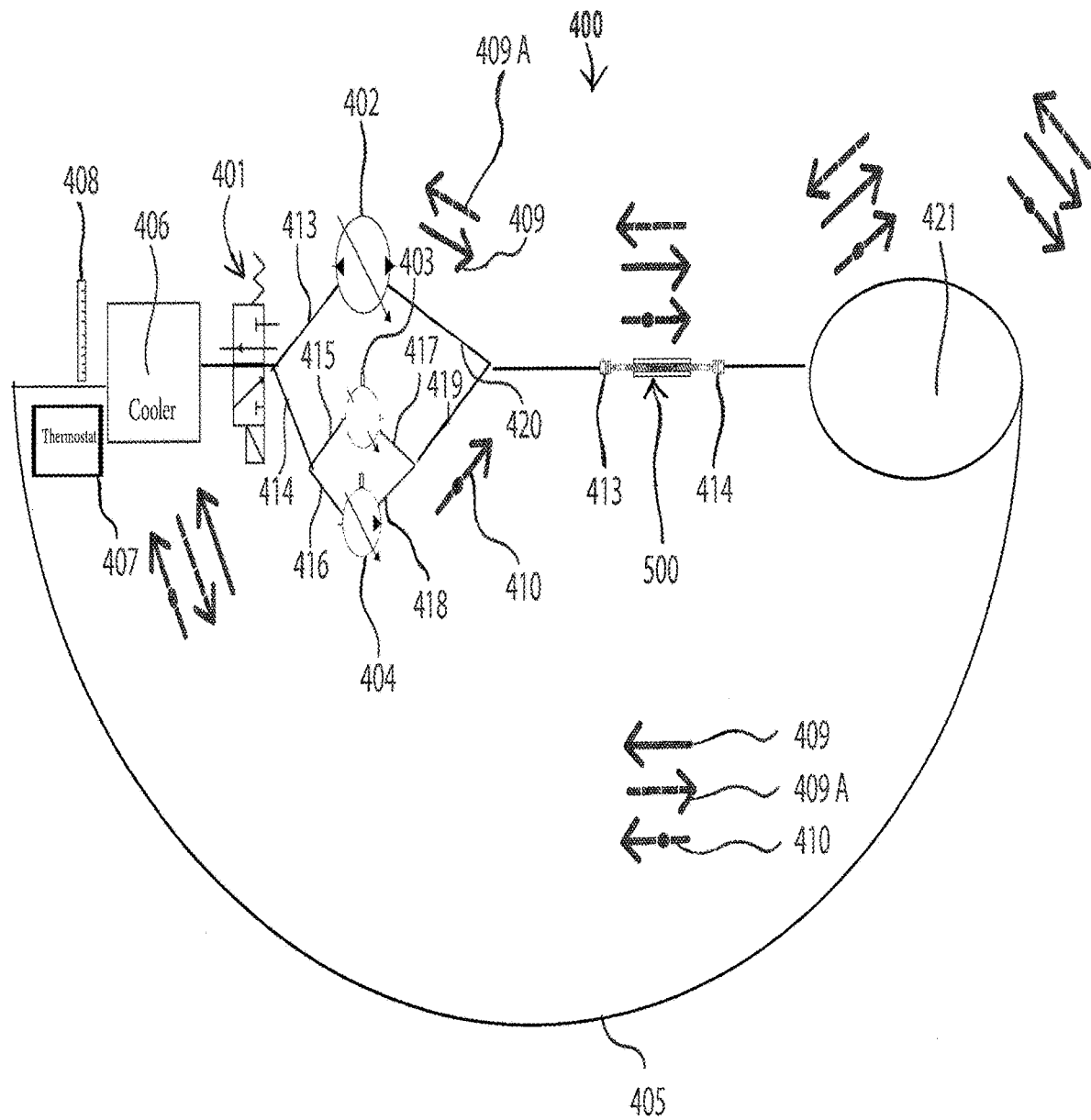

FIG. 4 shows the hydraulic circuit that allows to apply the tactile, vibro-tactile and cold stimuli and whose operation is controlled through a computer system through a PC and that comprises 3 hydraulic pumps, hoses and connections, 1 actuator, 1 cooler, 1 T ° sensor, 1 thermostat, one 3-way valve and 2 positions and another two 2 two-way and two positions all normally closed.

Figure 5:
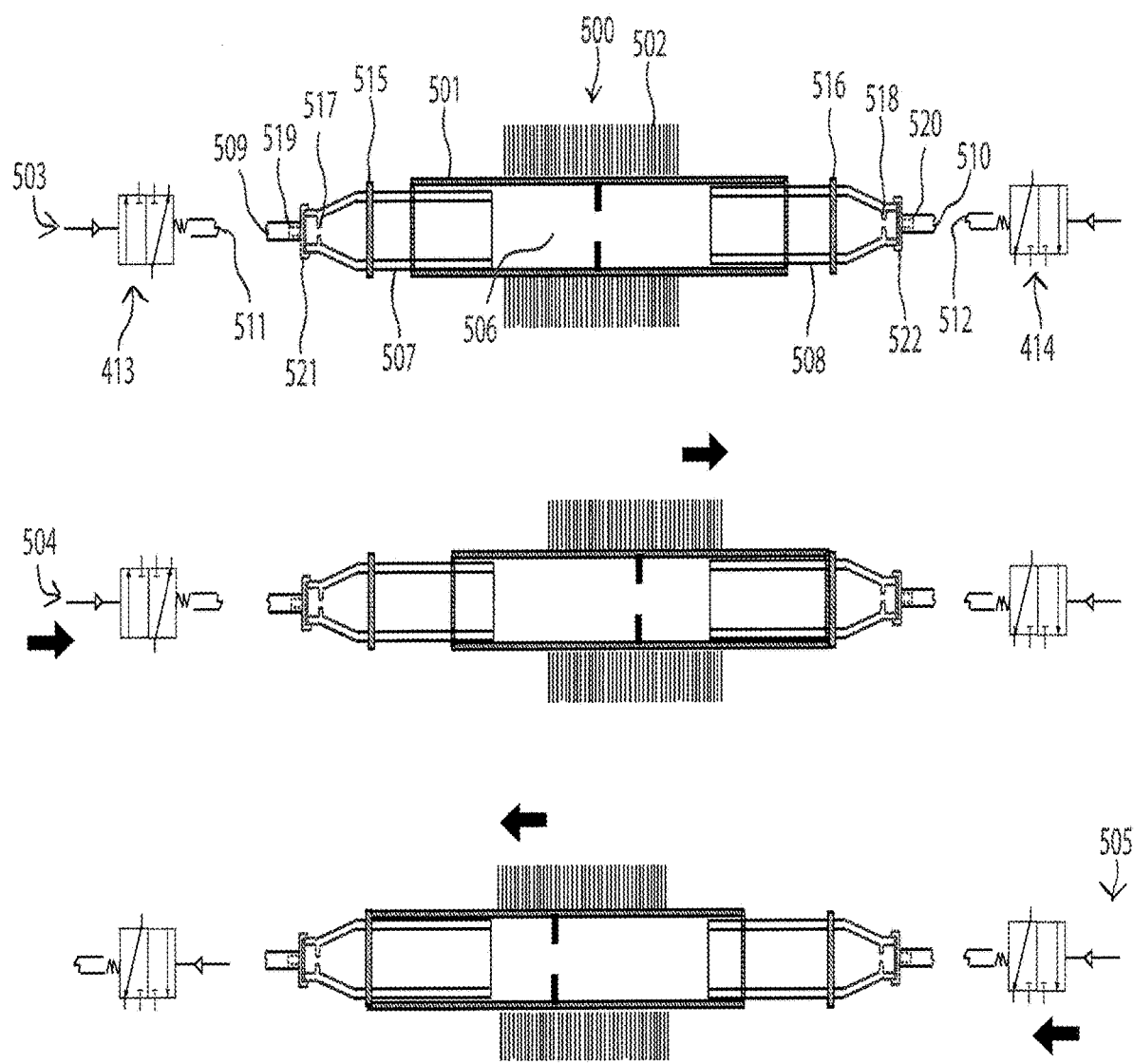

FIG. 5 shows an actuator that allows to apply tactile stimuli, caresses, on the cutaneous surface covering the upper part of the patient's spine, which is complemented by two, 2-way valves and 2 positions; one on each side of the actuator.

DETAIL DESCRIPTION OF THE INVENTION

The objective of this invention is to provide the equipment and the method to use it for the self-care of patients with chronic pain through frisson induction by means of actuators, including a hydraulic circuit with an actuator. Special mention within the stimuli used in this invention is occupied by music, since it has been shown to be the most efficient way of presenting sensory stimuli to elicit frissons and for this reason some of the tactile and visual stimuli have been synchronized with the music (multimodal stimulation).

Figure 1:
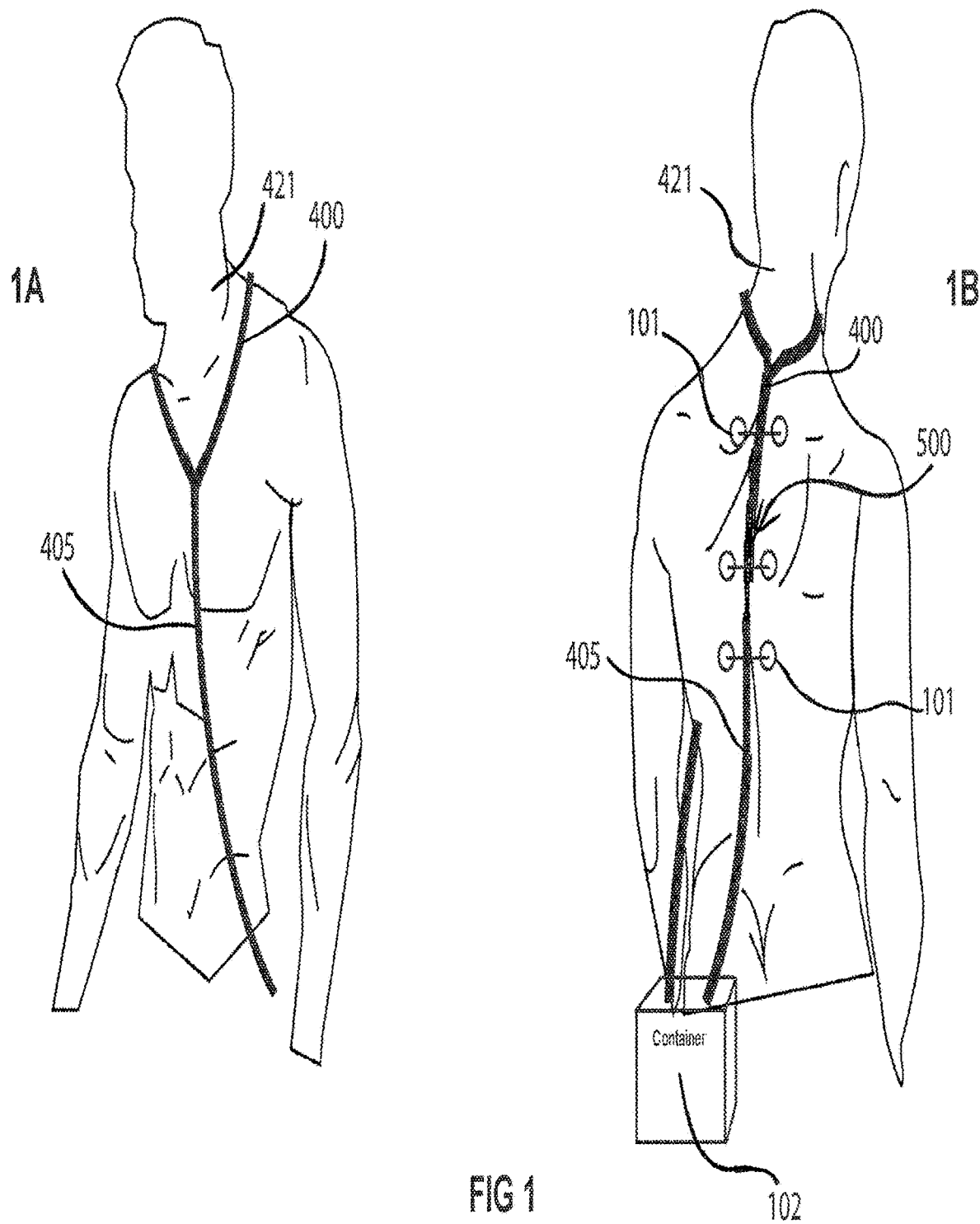

FIGS. 1A and 1B show how to use the hydraulic circuit (400), in shoulder strap, with the head in (421) and the flexible tube (405), surrounding the patient's back and allowing to elicit the stimuli and vibrotactiles of this invention. In the back of the patient the flexible tube FIG. 1B is attached to the skin by means of double suction cups (101), loose to maintain the vibration of the tube. The container on the patient's back (102) of FIG. 1B comprises part of the hydraulic circuit: the hydraulic pump, a 3-way valve, a temperature sensor and a cooler. The actuator (500) is located skimming the skin covering the upper part of the spine.

Figure 2:
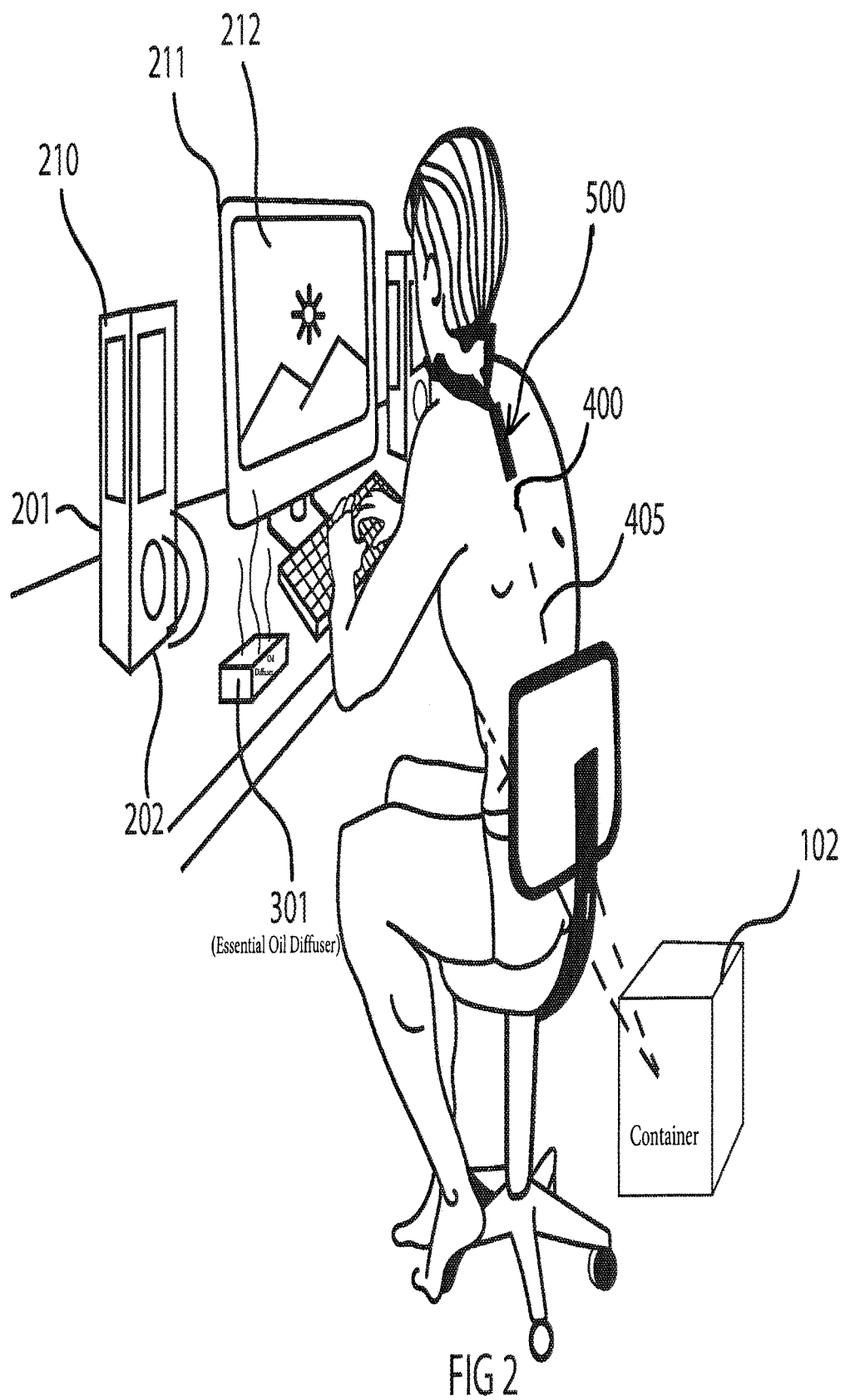
FIG. 2, shows the way to place the hydraulic circuit in the back of the patient in order to apply the tactile stimuli, vibrotactiles and cold, on the surface of the skin and muscles that cover the upper part of the spine.
Figure 3:
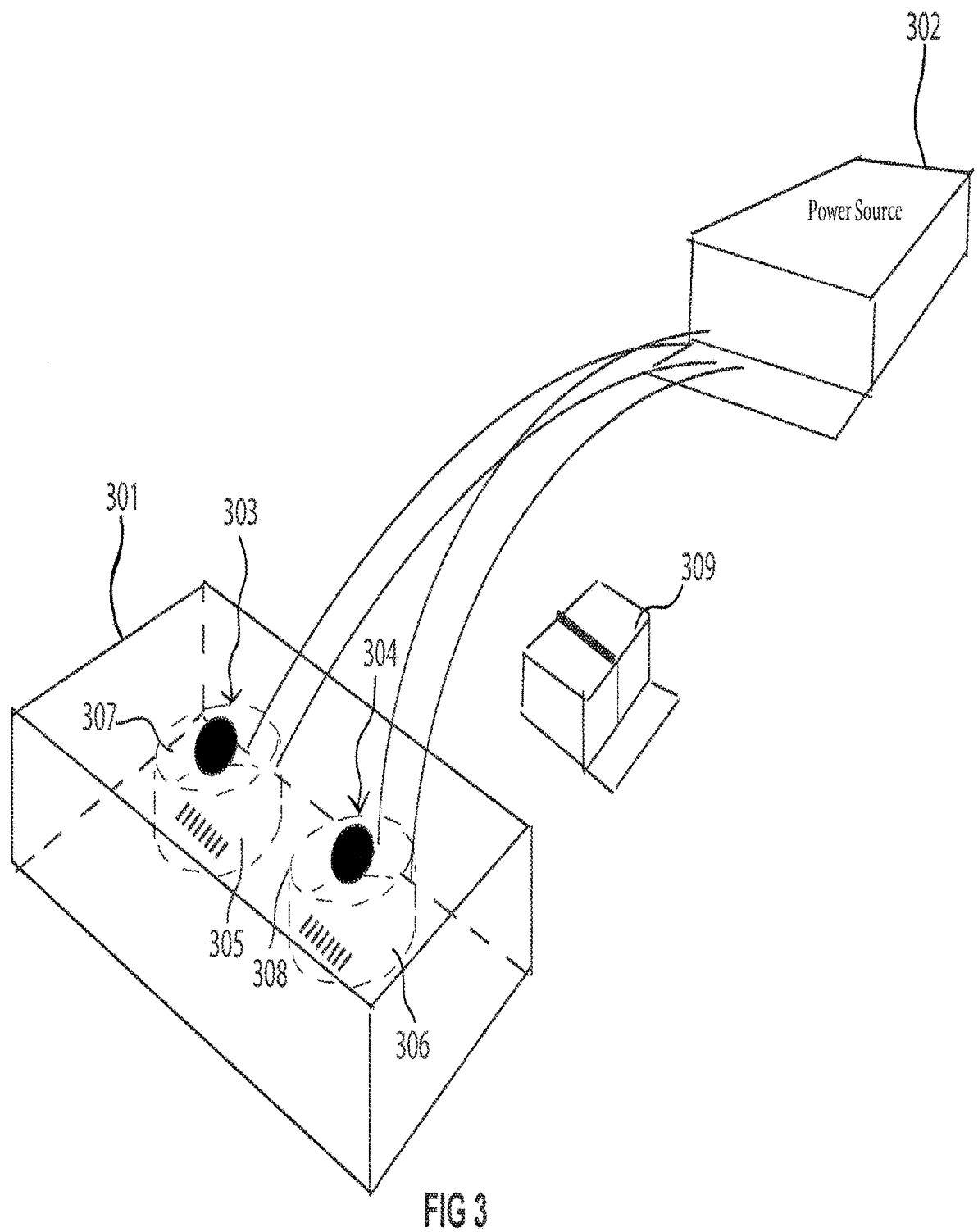
FIG. 3 shows a diffuser of essential oils, which has 2 circular containers, one for each oil, embedded in a textile fiber, together with a resistance, all inside a box with a straight parallelepiped shape and two holes in its upper face.

On the other hand, FIG. 2 shows the necessary hardware to elicit the necessary audiovisual stimuli to enhance the cold and vibrotactile stimuli caused by the hydraulic circuit described above. Hardware elements could be important to use virtual reality (VR) technology, but not having it, does not prevent the patient from experiencing the benefits of this invention.

Okechukwu O. et al (2011), define virtual reality technology (VR), as very interactive and based on a multimedia computing environment in which users participate in a world generated by computers. Virtual technology (VT) is the simulation of an imaginary environment in 3 dimensions that provides visual interactive experiences in real time, sounds, tactile sensations and other forms of feedback and is the technology necessary to implement VR. However, budgetary, technical or other constraints make it advisable to use this technology according to the preferences of the patients.

Virtual reality systems can be classified into 3 types; a) non-immersive, b) semi-immersive and c) totally immersive.

Virtual reality seeks to simulate sophisticated three-dimensional spaces, however for the purposes of the present invention, the non-immersive approach offers a virtual world, through a simple window on the desktop of the PC, on a high-resolution monitor. The non-immersive devices are lower cost and quickly accepted by users and can be improved with future investments.

There are several studies in which the use of virtual reality in rehabilitation in general and in the management of pain through the distraction techniques provided by VR has been studied. As an example, Shahrbanian S. et al (2012) made an extensive literature review and experiments to determine the effectiveness of this type of treatment in pain management. The authors concluded that the distraction techniques allowed by VR were a promising way to alleviate chronic pain in non-pharmacological treatments. The components to generate a virtual reality are divided into two types of components; hardware and software.

Hardware Components

Hardware comprises 5 subcomponents: work stations, accelerated processing cards, tracking systems and peripheral input and output devices:

Work stations: nowadays have a great development, especially in terms of CPU, graphics, memory capacity and are optimized for the visualization and manipulation of different types of information. The greater the RAM memory, the greater the efficiency of the computer.

Cards of accelerated processing: They allow to update the presentation of the peripheral devices of exit with new sensorial information, such as the graphics cards and of 3D sound.

Monitoring systems: These systems determine the position and orientation of the user in the virtual environment and are divided into mechanical, electromagnetic, ultrasonic and infrared technology.

Peripherals of sensory output: These devices are used to present a virtual world to the user and basically comprises, the monitor, glasses or virtual reality helmets and hearing aids for 3D audio.

Input peripherals: They are used to interact with the virtual environment and with the objects inside it, such as the keyboard, the mouse and others.

The monitor (211) should have a curved screen (not excluding), since it provides a visual experience with less distortion, more natural and that causes less eye fatigue in long sessions, than those of flat screen and with wide viewing angles. It should have a large screen (not excluding) and high resolution (not excluding), so that it is easier to work with graphics, video and multimedia.

Audio system: Unless you want to have a good sound, without using VR headsets, a good audio system (202) is required, which makes the therapies more immersive. A surround sound, greater clarity and deeper bass are the benefits of a good speaker system. For this purpose we must consider the cost, the frequency response, the power, the impedance, the sensitivity, the performance, the distortion and the directionality.

Software Components

The software comprises four subcomponents: 3D modeling, 3D graphics software, software to edit digital sounds and virtual simulation software:

3D modeling software, which allows you to build geometric objects in a virtual reality world and specify the properties of these objects.

2D graphic design software, to apply to the objects characteristics that improve the virtual details.

Software to edit digital sounds, which allow to mix and edit the sounds that the objects emit within the virtual reality environment.

VR simulation software that bring together all the components.

Software Suitable for this Invention

For the requirements of this invention a system based on C++ programming language was developed by adapting programs from the Arduino library, which contains pieces of code made by third parties.

To load our programs in Arduino or in another compatible card, the IDE (Integrated Development Environment) was downloaded. The IDE is the official Arduino application that allows you to program and download the program to our cards. With these programs the connections between the microcontroller and the sensors and actuators for this invention were done; The diffuser and the hydraulic circuit work alone or in parallel and can be synchronized or not with the audio and video of the computer. The microcontroller can be powered through the USB connection or with an external power supply in the present case with a power source.

Musical and Visual Stimuli

According to the previous references, the musical and visual stimuli that most effectively awaken emotions are pieces of classical music, melancholic music and videos of landscapes and natural life (201) and (212), respectively. There are many databases of images and videos available in multimedia, free or paid, that have been standardized and classified by gender, author, era and others to be used in psychological or other applications. As an example there are WEB pages of music, opera and other genres and videos of natural landscapes, natural fractals and in general scenes of natural life (eg on www.youtube.com).

Multimedia is a technology that allows to integrate text, number, graphics, still or moving images, animation, sounds and videos and also allows navigation along different documents. It refers to any object or system that uses multiple means of physical or digital expression to present or communicate information. The multimedia presentations can be viewed or heard on a stage, transmitted or played locally by means of a multimedia player, as understood by this invention. A transmission can be live or recorded and with analog or digital technology and the digital can be downloaded or transmitted in streaming.

By means of an example for the present invention one can use, among others, Windows Media Player (latest version 12), which is available for Windows 7, 8 and 10.

For Mac, Windows Media components can be downloaded so that QuickTime can play Windows Media files. In addition you can use free VLC Media Player which is a free and open source multimedia player, multiplatform and a framework that plays most multimedia files, as well as DVD, Audio CD, VCD and various transmission protocols.

Olfactory Stimuli

The odorants of this invention are presented through an essential oil diffuser (301) which is connected to a power source (302). The diffuser comprises a box with two holes which comprises two containers (303) and (304) among which are 2 resistors (305) and (306), in oil soaked in a cotton (307) and (308). The oil is released through the holes in the box when the resistance is heated, a process that is controlled from the PC through the Computational System.

For the control of the diffusers, a Wemos D1 mini card is used, which is responsible for activating/deactivating it, either individually (one container) or in parallel (both containers.) This is done from the PC by means of a relay module. With two channels (309) to allow the passage of the 24 V of a strip that in turn comes from the power source.

Vibrotactils

To present the vibrotactile stimuli an hydraulic circuit is used, closed and parallel, (400) that allows to massage with strokes and caresses and also apply cold and vibrations, to the cutaneous surface of the upper part of the patients' spine. The vibrations are caused by the turbulent flow generated by the peristaltic pump and the actuator, and transmitted to the tubes.

The circuit comprises 3 pumps, one peristaltic (402) moved by a stepper motor (DC, 24 V and 0.6 A) and 2 microdiaphragm pumps (403) and (404), (DC 12V and 1.5 A), flexible tubes (405), Y connections, a cooler with Peltier plates (406), a thermostat (407) and a temperature sensor (408), a micro mini three-way valve, two positions (401), normally closed (DC 12V and 185 mA), and an hydraulic actuator (500), which has two 2-way valves, 2 positions, normally closed, at both sides of it (413) and (414).

In turn, the hydraulic circuit comprises two parallel hydraulic half-circuits (409) and (410), functionally separated by the normally closed three-way solenoid valve (401) and wherein the operation of the first half-circuit (410) is controlled by a Arduino Nano microcontroller (A0), loaded with a program. The microcontroller simultaneously controls the activation of the two microdiaphragm solenoid pumps (403) and (404) and the opening of the three-way valve (401), through a 5V relay module and three channels, through a USB cable Android from the PC.

In short the operation of the first hydraulic half circuit (410) comprises the micro mini three-way solenoid valve, normally closed (401), which upon opening allows the flow to simultaneously go to the two microdiaphragm pumps (403) and (404), located in parallel and fed through two independent tubes (415) and (416), respectively, and which are born from one in common (414), coming from the cooler through the 3-way valve. The discharge of the fluid is done by two independent tubes (417) and (418) that are then joined together with a third one (419) that connects with the discharge tube of the peristaltic pump (420) and wherein the fluid that both microdiaphragm pumps drives through the tube (419), towards the cooler (406), is done to the rhythm of the music of the computer's multimedia player.

The Peltier plate cooler, with fans for each of them and water blocks, has a temperature sensor at its inlet, the readings of which can be seen on the PC screen. It also has an STC-1000 Digital Thermostat that is powered by the 220V of the home electric network and that is regulated independently. As programmed in the thermostat, the set of 3 Peltier cells and their respective fans will be activated/deactivated. The set of Peltier cells and fans are powered from a power supply o 12V and 40 A.

The functionality of this semicircuit is given by a sound sensor, capable of detecting an audible signal and converting it into a voltage signal, which is read by the analog input of the microcontroller.

The program musical_source_code or loaded in the microcontroller, performs an analysis of these signals by separating the high and low frequencies to activate the microdiaphragm pumps (outputs D12 and D13). The microdiaphragm pumps are controlled through an Android USB cable and a three-channel relay module (one for the valve) from the PC.

On the other hand and additionally, sets of LEDs are activated, FIG. 2, (210) to accompany the sounds (outputs D12, D13, D4 and D9, D10 and D11). The activation signals of the pumps are received by the L298 driver, which is responsible for activating and deactivating the pumps, giving them power from the 12 V power source.

The hydraulic semicircuit and LED lighting (210) works with any 2 instruments that have different sound frequencies (e.g. drum and flute). In summary, the hydraulic circuit of this Invention is similar to the hydraulic circuit of a musical water source.

The second of the semicircuits, has two modes of work, in the first (409) the flow has a unidirectional sense and in the second works alternately bidirectional (409) and (409A), due to the movement of advance and retraction of the engine step by step of the peristaltic pump, within a limited range, given by the lengths of its cylinder and plungers.

In the first mode of work, the micro mini three-way valve (401), shared by the half-circuits (409) and (410), opens to the second half-circuit (409), while the peristaltic pump is activated (402), which is fed through the tube (413) and discharges its flow in the tube (420) that connects to the tube (419) from the 2 diaphragm pumps (403) and (404). While the three-way solenoid valve (401) is still open and the peristaltic pump is working, the flow recirculates into the 2nd half-circuit to the Peltier plate cooler (406) and with the hydraulic actuator open in that direction FIG. 6, (623).

The functionality of this working mode of the second hydraulic semicircuit (409) is given by the Wemos D1 mini Card, mentioned above, which is responsible for controlling both the activation/deactivation of the peristaltic pump (402), as well as the speed of rotation of the same, the execution times of the same, the cycle restart times and the option to select random movements, speeds and times. This is done from the PC through an Android USB connection to the Wemos D1 mini card. By pin D3 the card sends the necessary pulses directly to the DAT Input of the driver (Kamoer). The activation/deactivation is also carried out by means of a one-channel relay, which controls the opening of the solenoid valve towards the peristaltic pump.

From the pin D6 of the Wemos Card, the activation/deactivation is carried out by means of a relay, to allow the passage of the 24 V necessary for the supply of the driver (Kamoer) of the peristaltic pump. The 24 V comes from the power source 24V, 10 A, which shares the voltage with the diffuser system by means of a power strip. One of the protoboard of the driver allows to have more feeds of 5 v and their respective earths (GND) to power the relay modules and share the GND lands with the driver (Kamoer) and the Wemos D1 mini card of the control of diffusers.

So that the patient does not have to operate the hydraulic circuit by default, in terms of motions and times, and above all to introduce uncertainty in the sensory experiences experienced, a randomization option was enabled in the execution program of this working mode (activate/deactivate in speed and time ranges). The randomness that the previously indicated variables, movement, velocities and times take, is obtained through a Random Value Generator Program that is in the Random library:

www.arduino.cc/reference/en/language/functions/random-numbers/random

Because Arduino is unable to create a true random number, the randomSeed library allows you to place a variable, constant, or other control function within the random function, and generate random numbers:

www.arduino.cc/reference/en/language/functions/random-numbers/randomseed/

As an alternative there are different programs that generate random variables, as an example in the following link you can find a program developed in C++:

www.cplusplus.com/reference/cstdib/rand/

The 2nd mode of the 2nd semicircuit (409) is intended to make a slight caress on the skin covering the upper part of the spine and is achieved through the work of an actuator (500), the 3-way solenoid valve and two positions (401) the two 2-way valves and 2 positions (413) and (414) and the stepper motor work of the peristaltic pump (402). The functionality of the stepper motor, which operates bi-directionally at a predetermined distance, is given by the Wemos D1 mini Card, mentioned above, which is responsible for controlling the peristaltic pump (402) and simultaneously activating/deactivating the mini micro three-way solenoid valve and the two 2 ways solenoid valves, using a 5V and 4-channel relay module, via an Android USB cable from the PC.

The hydraulic actuator FIG. 5, (500) consists of a cylinder (501) partially lined in a fabric with hairs (502), which starting from a central position (0503) and with an inner ring at the center (506), moves longitudinally and alternately in both directions and in the same distance (504) or (505), on a pair of plungers that are fixed and hollow, water circulates inside them (507) and (508), and ending in nozzles rings that point in opposite way (509) and (510), to both directions of the cylinder and discharging into the tubes of the hydraulic circuit (511) and (512) and wherein the actuator is alternately fed by water driven by the two solenoid valves, 2 ways and two positions (413) and (414), located on both of the cylinder. On the outside of each of the plungers and at the same distance from its narrow ends are located two rings (515) and (516) that can stop the advance of the cylinder towards both sides and where each of both pistons have at their distal ends two inner rings (517) and (518) and grooves on the outside to screw two tube connectors (519) and (520) that catch a mesh (521) and (522). The inner rings as well as the mesh are intended to generate turbulent flows and the distance traveled by the actuator in either direction must be equal to the angular distance that the motor travels step by step in the corresponding displacements.

The cycle is initiated when the 3-way solenoid valve (401) opens, the peristaltic pump (402) is activated, one of the two-way valves is opened (413) or (414) and drives the fluid to any of the nozzles (509) or (510), while it flows to the second nozzle, dragging the inner ring of the cylinder (506) to the fluid passage. The cycle is repeated in the opposite direction with the advance/return of the stepper motor of the peristaltic pump and the alternating opening of the 2-way solenoid valves (413) and (414).

REFERENCES

| UNITED STATES PATENTS | | | |
|---|---|---|---|
| 5,327,886 | A | 08/1992 | Chen-pang Chiu |
| 6,425,764 | B1 | 06/1997 | Ralph Lamson |
| 2007/0225781 | A1 | 03/2006 | Saadat V. y Eitherington L. |
| 2010/0312042 | A1 | 12/2010 | Anderson et al eb;normal |
| 7,927,294 | B2 | 04/2011 | Kamimura et al |

-continued

UNITED STATES PATENTS

| 8,738,142 | B2 | 05/2014 | F. Palermo y C. Castel Chris. |
| 9,849,206 | B1 | 11/2016 | Ming Jen Hsiao |

OTHER PATENTS

| CN 202822492 | U CN | 03/2011 | Chih-Kuo Liang |
| 102010047757 | B3 DE | 10/2010 | Bernd Basche |
| WO 2006/084921 | A1 | 02/2005 | Julio Ruiz et al |
| CN 205181749U | | 11/2015 | 姚春玲 y 夏飞飞 |

OTHER REFERENCES

Arjmand H. et al (2017): "Emotional Responses to Music: Shifts in Frontal Brain Asymmetry Mark Periods Mark Periods of Musical Change", Frontiers in Psychology.

Arrom M. (2015): "Rasgos de personaidad, estrategias de afrontamiento y dolor cronico en pacientes con fibromialgia", Tesis U. de las Baleares.

Banos R. et al (2012): "Positive mood induction procedures for virtual environments designed for eldery people", Interacting with Computers.

Blakemore S. et al (2000): "Why can't you tickle yourself", Neuroreport Vol. 11.

Blood A. J. and Zatorre R. J. (2001): "Intensely pleasurable responses to music correlate with activity in brain regions implicated in reward and emotion". Proc. Nat. Acad. Sci.

Bloomer C. et al (2014): "Stress responses due to application of audio or visual stimuli", J. of Advanced Student Science.

Boehme R. et al (2018): "Distinction of self-produced touch and social touch at cortical and spinal cord level", PNAS org. [0245]

Brochard R. et al (2008): "Evidence of beat perception via purely tactile stimulation". Brain Research 1223.

Bushnell M. C. (2013): "Cognitive and Emotional Control of Pain and its disruption in chronic pain", Neuroscience, Advance Online Publication.

Cacioppo J. and Tassinary L. (2007: "The Handbook of Psychophysiology, 3 Ed, Cambridge.

Calvert G., Spence C. and Stein B. Eds. (2004): "The Handbook of Multisensory Processes, Cambridge, MIT, 8 ed.

Chang Y C. et al (2015): "Short-term effects of self-massaje combined with home exercise on pain, daily activity, and autonomic function in patients with myofascial pain dysfunctions syndrome.", J. Phys Ther. Sci. 27.

Cheng X. et al (2017), "On-stream analysis of iron or slurry using laser-induced breakdown spectroscopy", Applied Optics, vol. 56.

Chesterton L S. et al (2002): "Skin temperature response to cryotherapy". Archives of Physical Medicine and Rehabilitation, 83.

Colver M. and El-Alayli (2015): "Getting aesthetic chills from music: The connection between openness to experience and frisson", Psychology of Music.

Costa P. (2015): "Modelling fragrance components release from a simplified matrix used in toiletries and household products", Industrial & Engineering Chemistry Research.

Craig D. G. (2005): "An exploratory study of physiological changes during "chills" Induced by music.", Music. Sci.

De Kort Y. et al (2006): "What's wrong with virtual trees? Restoring from stress in a mediated environment", J. of Environmental Psychology.

DeLeon I. and Iwata B. (1996): "Evaluation of a Multiple-Stimulus Presentation Format for Assessing Reinforcer Preferences", J. of Applied Behavior Analysis, 29.

Diette G. at al (2003): "Distraction Therapy With Nature Sights and Sounds Reduces Pain During Flexible Bronchoscopy", Chest, 123.

Dobek C. et al (2014): "Music modulation of pain perception and pain-related activity in the brain, brain stem and spinal cord", Journal of Pain.

Eckart S. (1974): "Temperature Regulation: The Spinal Cord as a Site of Extrahypothalamic Thermoregulatory Functions". Vol 71.

Edris A. (2007): "Pharmaceutical and Therapeutic Potential of Essential Oils and Their Individual Volatile Constituents: A Review". Phytotherapy Research, 21.

Edwards C. et al (2017): "Neuroestimulation Devices for the Treatment of Neurologic Disorders", Mayo Clinic Proceedings.

Ernst E. and Fialka V. (1994): "Ice freezes Pain?; A Review of the Clinical Effectiveness of Analgesic Cold Therapy", J. of Pain and Symptom Management.

Etzi R. et al (2018): "Stroking and tapping the skin: Behavioral and electrodermal effects", Experimental Brain Research.

Fernandez-Sotos A. at al (2016): "Influence of Tempo and Rhytmic Unit in Musical Emotion Regulation", Frontiers in Computational Neuroscience, August Field T. (2017) "Massage therapy research review", Complementary Ther. Clin. Pract. November Follman R. et al (2018): "Multimodal sensory information is represented by a combinatorial code in a sensorimotor system", PLOS Biology.

Fridja, N. (1999). "Moods, Emotion Episodes, and Emotions." En P. Ekman, y R. J. Davidson. (editors). The Nature of Emotion. Oxford University Press: New York.

Gay-Balmaz and Putkaradze V. (2018) "Geometry theory of flexible and expandle tubes conveying fluid: equations, solutions and shock waves." Physics, Flu-Dyn.

Garza-Villarreal E. et al (2017): "Music-Induced Analgesia in Chronic Pain Conditions: A Systematic Review and Meta-Analysis", Pain Physician.

Gladwell V. et al (2012) "The effects of views on nature and autonomic control", Eur. J. Appl. Physiol. 112.

Gold J L. and Watanabe T. (2010): "Perceptual Learning", Curr Biol., January

Goldstein, A. (1980): "Thrills in response to music and other stimuli". Physiological Psychology, 8.

Goldstein S. and Casanefia L. (2010): "Foundations of Massage", Cap. 16, Lisa Casanelia y David Stelfox, 3 Ed. Editors Churchill and Livingstone, Elsevier.

Grewe O. et al (2007): "Listening to music as a re-creative process: Physiological, psychological and psychoacoustic correlates of chills and strong emotions.", Music Perception, 24.

Grewe O. et al (2010): "Chills in different sensory domains: Frisson elicited by acoustical, visual, tactile and gustatory stimuli". Psychology of Music, 39.

Grinde B. and Grindal G. (2009): "Biophilia: Does Visual Contact with Nature Impact on Health and Well-Being?.", Int. J. Environ. Res. Public. Health, 6.

Gross J. and Thompson R. (2007): "Emotion Regulation: Conceptual foundations", Handbook of Emotion Regulation. New York Guildford Press.

Hanjalic K and Launder B. (1972). "A Reynolds stress model of turbulence and its application to thin shear flows", Journal of Fluid Mechanic.

Harrison L. and Loui P. (2014): "Thrills, chills, frissons and skin orgasms: towards an integrative model of transcendent psychophysiological experiences in music". Frontiers in Psychology.

Harvey L. (1992): "The critical operating characteristics and the evaluation of expert judment", Organization Behavioral and Human Decision Processes, 53.

Haze S. et al (2002): "Effects of fragrance inhalation on symphatetic activity in normal adults", Japan. J. Pharmacol., 90.

Holden R and Holden J. (2013): "Out of Hours Music", British Journal of General Practice.

Holmes N. P et al (2009): "Multimodal Integration", Binder M. D. Hirokawa N.-J. y Womans E. (2016): "The effects of Music on Pain a Meta-Analysis", J. of Music Therapy.

Huang J. et al (2013): "Feeling Music: Integration of Auditory and Tactile Inputs in Musical Meter Perception", Adv. Exp. Med. Biol. 787.

Hyung J. (2016): "The effects of Music on Pain: A Meta-Analysis", J. of Musical Therapy.

James K. (2018): "The Handbook of Multimodal Multisensory Interfaces Vol 1: Foundations and User Modeling and Modeling and Common Modality Combination", Ed. Morgan and Claypool.

Juslin P. and Vastfjall D. (2008): "Emotional responses to music: The need to consider underlying mechanisms", Behavioral and Brain Science, 31.

Juslin P. et al (2008): "An Experience Sampling Study of Emotional Reactions to Music: Listener, music and situation.", Emotion 8.

King A. (2005): "Multisensory Integration: Strategies of Synchronization", Dispatch.

Koelsch S. and Jancke L. (2015): "Music and the heart", European Heart Journal, 10.

Koole S. (2009): "The psychology of emotion regulation: An integrative review", J. Cognition and Emotion".

Laird D. (1985): "Approaches to training and development", Reading Mass: Addison-Wesley.

Lakhan S. et al (2016): "The Effectiveness of Aromatherapy in Reducing Pain: A systematic Review and Meta-Analysis", Pain Research and Treatment.

Lee J. et al (2011): "Effect of forest bathing on physiological and psychological responses in Young Japanese male subjects", Public Health.

Louis M. and Kowalsky S. (2002): "Use of aromatherapy with hospice patients to decrease pain, anxiety, and depression and to promote and increased sense of wellbeing." Am J. Hosp. Pall. Care.

Malamud-Kessler C. et al (2014), "Fislologia de la vibracion", Rev. Mex. Neuroci. May-June 2014.

Melzack R. and Wall P. (1965): "Pain mechanisms: a new theory", Science (11).

Mills S. et al (2016): "identification and Management of Chronic Pain in Primary Care: A Review", Curr. Psychiatry Rep".

M M Tse et al (2002): "The effect of visual stimuli on pain threshold and tolerance", J. of Clinical Nursing.

Noy D. et al (2017): "Audiovisual integration increases the intentional step synchronization of side-by-side walkers", "Human Movement Science, 56.

Okechukwu O. (2011): "Understanding Virtual Reality Technology: Advances and Applications", Research Gates Publications.

Park B. and Kim S. (2013): "Cooling the Skin: Understanding a Specific Cutaneous Thermosensation", Journal of Lifestyle, Vol 3.

Piaget J. (1947): "Laformation de symbole: Limitation, jeu et rove, image et representation". Neuchatel: Delachaux et Nestle".

Plutchick R. and Kellerman H. (1980): "Emotion: Theory, Research, and Experience", Academic Press, Elsevier.

Poenaru D. et al (2016): "Local Application of Vibration in Motor Rehabilitation:Scientific and Practical Considerations", J. of Clinical Medicine.

Rastogi A. (2018): "Physiological effects of cryotherapy: A systemic Review", Indian J. of Applied Research" Volume 8, May 2018.

Recanzone G. (2009): "Interactions of Auditory and Visual Stimuli in Space and Time", Hear Research, 258.

Reynolds, Osborne, 1895: "On the Dynamical Theory of Incompressible Viscous Fluids and the Determination of the Criterion." Philosophical Transactions of the Royal Society of London. A, v. 186

Rios E. et al (2017): "Self-massage and Autonomic Response: Future Direction", Journal of Exercise, Sport and Orthopedics.

Rodica F. et al (2011): "Emotions induced by operatic music: Psychophysiological effects of music, plot and acting, A scientist's tribute to Maria Callas", Brain and Cognition 76.

Rolston A. and Lloyd-Richardson (2018): "What is emotion regulation and how do we do it ?," Self-Injury and Recovery, Cornell Research Program.

Roy M. et al (2008): "Emotional Valence Contributes to Music-Induced Analgesia", Pain 134.

Salimpoor V. et al (2009): "The Rewarding Aspects of Music Listening Are Related to Degree of Emotional Arousal", PlosOne.

Sawkut R. (2010): "Learning Theories: A Review", Oxford Business and Economics Conference Program.

Schneider R. (2018): "Medical aromatheraphy revisited—Basic mechanisms, critique and a new development", Hum. Psychopharmacol. Clin Exp.

Seah S. and Griffin M. (2006): "Normal values for the thermotactil and vibrotactil threshold in males and females" Int Arch Ocupp Environ Health.

Sergeant D. and Himonides E. (2016): "Gender and Music Composition: A Study of Music, and the Gendering of Meanings", Frontiers of Psychology.

Sena K. (2013): "A Systematic Review on the Neuronal Effects of Music on Emotion Regulation: Implications for Music Therapy Practice." Journal of Music Therapy 50 (3).

Shahrbanian S. et al (2012): "Use of virtual reality (inmersive vs non immersive) for pain management in children and adults: A systematic review of evidence from randomized controlled trials". Pelagia Research Library.

Shaygan M. et al (2017): "Valence and arousal value of visual stimuli and their role in the mitigation of chronic pain: What is the power of pictures?" J. of Pain 18(2).

Simons L. (2014): "Psychological processing in chronic pain: A neural systems approach", Neuroscience and bio-behavioral Reviews.

Skinner, B. F. (1938). "The behavior of organisms: an experimental analysis", Oxford, England: Appleton-Century.

Smith K. and Zhu L. (2010): "Theoretical evaluation of a simple cooling pad for inducing hypothermia in the spinal cord following traumatic injury", Med. Biol. Eng. Comput. 48.

Sowndhararajan K. and Kim S. (2016): "Influence of Fragances of Human Psychophysiological Activity: With Special Reference to Human Electroencephalographic Response", Scientia Pharmaceutica.

Subramian R. (2014): "Heat Transfer in Flow Through Conduits", Clarkson University, A. F. Mills.

Sutton S. et al (1965): "Evoked-Potential Correlates of Stimulus Uncertainty", Science Vol 150.

Takabatake S. et al (1988); "Peristaltic pumping in circular cylindrical tubes: a numerical study of fluid transport and its efficiency", J. Fluid Mechanic, v 193.

Tang N. et al (2008): "Effects of mood on pain responses and pain tolerance: An experimental study in chronic back pain patients", Pain 138.

Triberti S. et al (2014): "Psychological factors influencing the effectiveness of virtual reality-based analgesia: A systematic review", Cyberpstychol Behav Soc. Netw. 6.

Turk D. and Wilson H. (2010): "Fear of Pain as a Prognostic Factor in Chronic Pain: Conceptual Models, Assessment, and Treatment Implications", Curr. Pain. Headache. Rep. April.

Uher I. et al (2018): "Vibration Therapy and its Influence on Health", Biomedical, July 2018.

Uhlig S. et al (2013): "Effects of Music on Emotion Regulation: A Systematic Literature Review". Proceedings of 3' International Conference on Music and Emotion.

Ulrich R. S. et al (1991), "Stress recovery during exposure to natural and urban environments", J. Environ. Psychology, 11.

Verduyn, P., & Lavrijsen, S. (2015). "Which emotions last longest and why: The role of event importance and rumination", Motivation and Emotion, 39(1).

Vuoskoski J. and Eerola T. (2011): "The role of mood and personality in the perception of emotions represented by music". ScienceDirect, Elsevier.

Wilcox D. C. (2008): "Formulation of the k-omega Turbulence Model Revisited", AIAA Journal, Vol. 6

Yuan-Chi Lin et al (2017): "Using Integrative Medicine in Pain Management an Evaluation in Pain Management: An Evaluation of Current Evidence", Anesth. Anal; 125.

Zatorre R and Salimpoor V. (2013): "From perception to pleasure: music and its neural substrates", Proc. Natl Acad. Sci. USA.

Zentner M., Grandjean D. and Scherer K. (2008): "Emotions Evoked by Sound of Music: Characterization, Classification and Measurement". Emotion, Vol 8.

What is claimed is:

1. A method for a treatment of patients of chronic pains, the method comprising the following steps:
   evaluate a patient, through psychometric, sensory and physiological tests, psychological constructs, anxiety and fear, and a mood caused by an experience of pain;
   evaluate by means of a self-report of physical capabilities of the patient and by means of one or more instruments measuring blood pressure, heart rate, and electrical conductance of skin of the patient for informing the patient about physiological parameter values that should be achieved;
   select a sensory stimuli the patient will receive, wherein the sensory stimuli includes a combination of two or more of audiovisual, tactile, vibrotactic, and cold stimuli, and wherein one or more of an intensity, density, duration, volume, and frequency of the sensory stimuli is based on an emotional state of the patient;
   provide a work station having a computer, a corresponding monitor, and speakers or hearing aids, wherein the work station is configured to reproduce multimedia files presenting the audiovisual stimuli;
   connect the patient to a closed hydraulic circuit wherein the closed hydraulic circuit presents a tactile, vibrotactic, and cold stimuli to the patient; and
   provide an operational computer program that automatically executes a computer application on the computer and is configured to:
   induce frissons in the patient by means of the sensory stimuli and alter a behavior, functionality of senses, reflexes or physiological parameters of the patient;
   apply the sensory stimuli to the patient in a multisensory way, wherein a combination of different sensory stimuli are used to provide a set of sensations to the patient;
   apply the sensory stimuli to the patient in a multimodal way, wherein the set of sensations from the combination of different sensory stimuli are integrated;
   synchronize an application of a time and movement of the sensory stimuli with a rhythm of music.

2. The method according to claim 1, wherein the step of evaluating the experience of pain and the step of evaluating the self-report of physical capabilities of the patient comprises evaluating intensity, character, location, irradiation, time, associated factors, implications and meaning.

3. The method according to claim 1, wherein the step of selecting the sensory stimuli the patient will receive comprises invoking, provoking, measuring, analyzing and interpreting a reaction of the patient to the different sensory stimuli.

4. The method according to claim 1, wherein the step of evaluating the patient comprises evaluating one or more of the following cognitive skills of the patient: divided attention, selective attention, sustained attention, numerical reasoning, visual exploration, flexibility, inhibition, spatial memory, contextual memory, short-term memory, working memory, visuospatial memory, short-term visual memory, auditory perception, spatial perception, visual perception, planning, reasoning, problem solving, speed reaction time and processing speed.

5. The method according to claim 1, wherein the sensory stimuli include in the combination of two or more: chemical stimuli, electrochemical stimuli, physical stimuli, biological stimuli, physiological stimuli, vibratory stimuli, pressure and tension stimuli, movement stimuli, temperature stimuli, liquid stimuli, gaseous stimuli, light stimuli, and sound stimuli.

6. The method according to claim 1, wherein the rhythm of music is within one of the following musical genres: classical music, opera, film music, ballads and melancholic melodies, military marches, bossa-nova, sweeps of scale; and wherein the rhythm of music comes from the speakers that are in the work station.

7. The method according to claim 1, wherein a visual stimuli of the audiovisual stimuli comprises images of relatives of the patient and of nature, wherein images of nature include landscapes, rivers, seas, waves, forests, and gardens, and wherein the images come from the monitor of the work station.

8. The method according to claim 1, wherein the closed hydraulic circuit comprises three hydraulic pumps being a peristaltic pump and two diaphragm pumps, one hydraulic actuator, one cooler, one temperature sensor, one thermostat and three solenoid valves normally closed wherein one of the three solenoid valves is a three way valve and two of the three solenoid valves is a two way valve and wherein the closed hydraulic circuit is configured to be deployed around a torso of the patient in a bandolier, from shoulder to opposite hip and wherein the three pumps, the cooler, the temperature sensor, the thermostat and the three way solenoid valve are in a container, while a part of a flexible tube, the hydraulic actuator and the two-way solenoids valves are rubbing an area of the skin that covers an upper part of a spine and in which the flexible tube is loosely supported to the skin by means of double suction cups, so as to maintain a vibration of the tube.

9. The method according to claim 8, wherein a Peltier plate module has a temperature sensor and a digital thermostat at an inlet, wherein readings of the temperature sensor and the digital thermostat are on the monitor.

10. The method according to claim 8, wherein the peristaltic pump and the hydraulic actuator of the hydraulic circuit, cause a turbulent flow and vibrations that are transmitted to walls of tubes that are configured to present vibrotactile stimuli to an area of the skin that covers an upper part of the spine.

11. The method according to claim 8, wherein the operation of the hydraulic circuit that presents the tactile, vibrotactile and cold stimuli is controlled through the operational computer program on the computer.

12. The method according to claim 8, wherein the hydraulic circuit that presents the tactile, vibrotactile and cold stimuli is operated randomly from the computer in terms of time and velocity of the peristaltic pump.

13. The method according to claim 8, wherein the hydraulic circuit comprises two parallel half-circuits, functionally separated by the closed three-way solenoid valve and wherein the opening of the three-way solenoid valve and activation of two microdiaphragm solenoid pumps are simultaneously controlled.

14. The method according to claim 8, wherein a discharge of the two diaphragm pumps is done by a pair of independent tubes which are then joined with a third tube that connects to a discharge of the peristaltic pump and wherein fluid that both microdiaphragm pumps drive through the tube, towards the cooler, is driven to the rhythm of music in combination with operation of two LED lamps in the work station.

15. The method according to claim 8, wherein a functionality of a semicircuit is given by detecting audible signals and convert them into voltage signals and wherein a program performs an analysis of the voltage signals by separating high and low frequencies to activate microdiaphragm pumps and wherein the diaphragm pumps of the semicircuit, and the LED lamps work with at least two different sound frequencies and wherein a second semicircuit has two modes of operation, in the first a flow has a unidirectional direction and in the second the flow works alternately in a bidirectional way, due to a forward and backward movement of a stepper motor of the peristaltic pump, within a limited range, given by lengths of a cylinder and pistons of the hydraulic actuator.

16. The method according to claim 15, wherein the second mode of operation of the second semicircuit is configured to make a caress on the skin of the patient covering an upper part of the spine and that is achieved through the hydraulic actuator, the three-way solenoid valve and two positions and the two two-way solenoid valves, with a bi-directional work of the stepper motor of the peristaltic pump, and wherein the stepper motor operates bidirectionally at a given distance simultaneously with controlling activation and deactivation of the mini micro solenoid valve of the three way valve and of the two way valves.

17. The method according to claim 8, wherein in a first working mode a three-way micro mini-valve, shared by half-circuits, opens to a second half-circuit, while activating the peristaltic pump, which is fed through a tube and discharges a flow into a second tube that connects to the tube from the two diaphragm pumps, while the three-way solenoid valve continues open and the peristaltic pump is working, the flow recirculates into the second semi-circuit to a Peltier plate cooler and with the hydraulic actuator open in a direction of the flow.

18. The method according to claim 17, wherein the functionality of this first working mode of the second half-circuit is given by controlling both an activation and deactivation of the peristaltic pump, as well as a rotation speed of the peristaltic pump, execution times, cycle restart times and an option to select movements, speeds and random times through the computer and wherein the activation and the deactivation is also carried out, by means of a relay of a channel, which controls the opening of a solenoid valve towards the peristaltic pump.

19. The method according to claim 8, wherein the hydraulic actuator comprises a cylinder partially lined in faux fur fabric that is configured to touch the skin of the patient, and that starting from a central position and with a ring internal to a center, moves longitudinally and alternately in both directions and in the same distance, on a pair of plungers that are fixed in position and are hollow, water circulates inside the pair of plungers, and ending in ringed nozzles pointing in opposite directions, towards both ends of the cylinder and discharging into the hydraulic circuit tubes and wherein the hydraulic actuator is alternately powered by water driven by a flow of water through the two two-way solenoid valves located on sides of the cylinder and wherein on an outside of each of the plungers, at equal distance from narrow ends of each of the plungers, are located two rings that act as stops and brakes advancement of the cylinder to both sides and wherein each of both plungers have two inner rings threaded ends on the outside to screw two tube connectors that trap a mesh and wherein by geometry of inner rings of the plungers, as well as the mesh, generate turbulent flows and wherein the distance traveled by the hydraulic actuator in either direction must be equal to an angular distance traveled by a stepper motor in the corresponding displacements.

20. The method according to claim 1 wherein odorants of this invention are presented through an essential oil diffuser which is connected to a power source and wherein the diffuser comprises a box with two orifices which comprises two containers and two resistors with one resistor of the two resistors in each container of the two containers, and cotton soaked in oil from the essential oil diffuser and wherein the oil is released, through holes of the box, when the resistors heats up, a process that is controlled from the computer by the operational computer program to control activating and deactivating the diffusers, either individually, in one container, or in parallel with two containers, which is done from the computer through a two-channel relay module.

\* \* \* \* \*